US012564562B2

(12) United States Patent
Zhang et al.

(10) Patent No.: US 12,564,562 B2
(45) Date of Patent: Mar. 3, 2026

(54) INJECTABLE EPINEPHRINE FORMULATIONS DEMONSTRATING STABILITY OVER TIME

(71) Applicant: Amphastar Pharmaceuticals, Inc., Rancho Cucamonga, CA (US)

(72) Inventors: Jack Yongfeng Zhang, Diamond Bar, CA (US); Mary Zi-ping Luo, Diamond Bar, CA (US); Fonda Su, Hacienda Heights, CA (US); Marvin Lin, Temple City, CA (US); Jie Fei Ding, Diamond Bar, CA (US); Justin Jun Wei, Chino Hills, CA (US); Wenbo Yu, Arcadia, CA (US); Rong Zhou, Brea, CA (US)

(73) Assignee: Amphastar Pharmaceuticals, Inc., Rancho Cucamonga, CA (US)

( * ) Notice: Subject to any disclaimer, the term of this patent is extended or adjusted under 35 U.S.C. 154(b) by 651 days.

(21) Appl. No.: 17/976,111

(22) Filed: Oct. 28, 2022

(65) Prior Publication Data

US 2023/0140033 A1 May 4, 2023

Related U.S. Application Data

(63) Continuation-in-part of application No. PCT/US2021/047673, filed on Aug. 26, 2021.

(60) Provisional application No. 63/070,600, filed on Aug. 26, 2020.

(51) Int. Cl.

| | |
|---|---|
| ***A61K 31/137*** | (2006.01) |
| ***A61K 9/00*** | (2006.01) |
| ***A61K 9/08*** | (2006.01) |
| ***A61K 47/02*** | (2006.01) |
| ***A61K 47/12*** | (2006.01) |
| ***A61K 47/18*** | (2017.01) |

(52) U.S. Cl.

CPC .......... *A61K 31/137* (2013.01); *A61K 9/0019* (2013.01); *A61K 9/08* (2013.01); *A61K 47/02* (2013.01); *A61K 47/12* (2013.01); *A61K 47/183* (2013.01)

(58) Field of Classification Search

CPC .................................................... A61K 31/137

USPC .......................................................... 514/653

See application file for complete search history.

(56) References Cited

U.S. PATENT DOCUMENTS

| | | | | |
|---|---|---|---|---|
| 9,119,876 | B1 * | 9/2015 | Kannan | A61P 37/08 |
| 9,283,197 | B1 | 3/2016 | Taneja | |
| 9,295,657 | B1 | 3/2016 | Kannan et al. | |
| 10,004,700 | B1 | 6/2018 | Taneja | |
| 10,039,728 | B1 | 8/2018 | Taneja | |
| 10,130,592 | B2 | 11/2018 | Vinayagam et al. | |
| 10,624,864 | B2 | 4/2020 | Sanghvi et al. | |
| 10,688,044 | B2 | 6/2020 | Hartman et al. | |
| 11,337,938 | B2 | 5/2022 | Sanghvi et al. | |
| 2008/0139664 | A1 | 6/2008 | Yeboah et al. | |
| 2017/0189352 | A1 | 7/2017 | Sanghvi et al. | |
| 2018/0250245 | A1 | 9/2018 | Sanghvi et al. | |
| 2019/0105288 | A1 | 4/2019 | Sanghvi et al. | |
| 2020/0206163 | A1 | 7/2020 | Sanghvi et al. | |
| 2020/0268689 | A1 | 8/2020 | Surakitbanharn | |
| 2021/0154157 | A1 | 5/2021 | Surakitbanharn | |
| 2021/0205238 | A1 | 7/2021 | Augustin et al. | |
| 2021/0361595 | A1 | 11/2021 | Hartman et al. | |

FOREIGN PATENT DOCUMENTS

| | | |
|---|---|---|
| WO | WO2019162892 | 8/2019 |
| WO | WO2022046976 | 3/2022 |

OTHER PUBLICATIONS

International Search Report and Written Opinion for PCT/US21/47673 dated Oct. 29, 2021, 11 pages.

Notice of Allowance for U.S. Appl. No. 16/817,253 dated Oct. 7, 2021, 8 pages.

Response to Office Action for U.S. Appl. No. 16/817,253 dated Mar. 17, 2021, 7 pages.

* cited by examiner

*Primary Examiner* — Jeffrey H Murray
*Assistant Examiner* — Rilla Marie Samsell
(74) *Attorney, Agent, or Firm* — IceMiller LLP

(57) ABSTRACT

Disclosed herein are pharmaceutical formulations including epinephrine that have increased epinephrine retention over long-term storage, e.g., 30-months. In one aspect, a formulation includes: one or more of 0.1 mg/mL of epinephrine or a pharmaceutically acceptable salt thereof provided without any overage, a tonicity regulating agent including 8.2 mg/mL of sodium chloride, a pH adjusting agent including a mixture of 1.5 mg/mL sodium citrate dihydrate, 3.3 mg/mL of citric acid monohydrate, and, optionally, an as-needed amount of sodium hydroxide to maintain the pH level of the formulation within a range of 3.6 to 4.0, 0.075 mg/mL of sodium metabisulfite, and 4 μg/mL of ethylene diamine tetra-acetate disodium. The formulation has an API recovery of 94.5% or more after at least 30 months of storage at long-term storage conditions defined as 25° C.±2° C. at 1 atmosphere. In addition, in another aspect, a formulation includes 1 mg/mL of epinephrine and other ingredients.

21 Claims, 15 Drawing Sheets

Epinephrine Sulfonic Acid (ESA) (Impurity F) (%) (w/w) vs. Duration (Months)
(Solution Including 0.1 mg/mL EPI & 1 mg/mL Sodium Bisulfite stored at 25°C ± 2°C)

Example 17: y = 0.9013x + 0.5486
Example 18: y = 0.8299x + 0.6036
Example 19: y = 0.8724x + 0.6407

——— Example 17      ········· Example 18      - - - - Example 19

Active Pharmaceutical Ingredient (API) Recovery (EPI) (%) (Assay) vs. Duration (Months)
(Solution Including 0.1 mg/mL EPI & 1 mg/mL Sodium Bisulfite stored at 25°C ± 2°C)

Duration (Months)

Example 17    Example 18 - - - Example 19

L-Epinephrine (%) (Assay) vs. Duration (Months)
Various Antioxidant (Sodium Metabisulfite) Concentration Levels at 40 °C

| 40°C | mg/ml | Equation |
|---|---|---|
| Ex. 23 | 0.04 | y=-0.015x + 0.9945 |
| Ex. 24 | 0.08 | y=-0.0145x + 0.9945 |
| Ex. 25 | 0.46 | y=-0.02x + 0.9918 |

Legend:
● 0.04 mg/ml
◆ 0.46 mg/ml
—— Linear (0.08 mg/ml)
● 0.08 mg/ml
—— Linear (0.04 mg/ml)
······ Linear (0.46 mg/ml)

Predicted EDTA-Bound Zinc vs. Human Absorbed Zinc

(%) EDTA-Zinc Binding Levels Relative to Min. Lower and Max. Upper Human Zinc Absorption per EDTA (µg/ml) Loading Levels EDTA (µg/ml)

INJECTABLE EPINEPHRINE FORMULATIONS DEMONSTRATING STABILITY OVER TIME

CROSS REFERENCE TO RELATED APPLICATIONS AND INCORPORATION BY REFERENCE TO ANY PRIORITY APPLICATIONS

The present application claims the benefit of priority to and is a Continuation-in-Part of International Patent Application No. PCT/US2021/047673, published as WO 2022/046976, filed Aug. 26, 2021, which claims the benefit of priority to U.S. Provisional Patent Application No. 63/070,600, filed Aug. 26, 2020, the entireties of which are both hereby incorporated by reference herein. Any and all applications for which a foreign or domestic priority claim is identified in the Application Data Sheet as filed with the present application are hereby incorporated by reference under 37 CFR 1.57.

FIELD

The present disclosure relates to epinephrine formulations including epinephrine as the active pharmaceutical ingredient ("API"); and, more particularly to one or more epinephrine formulations with a relatively low dosage level of epinephrine provided without any overage, which demonstrate increased API retention for up to 30 months of storage.

BACKGROUND

Epinephrine, also known as adrenaline or catecholamine; is a medication and hormone produced by the adrenal gland, located above each kidney. Epinephrine is chemically described as -3,4-Dihydroxy-α-[(methyl-amino) methyl] benzyl alcohol, has a molecular formula is $C_9H_{13}NO_3$, and a molecular weight (M.W.) of 183.2 g/mol. Epinephrine has the following structural formula:

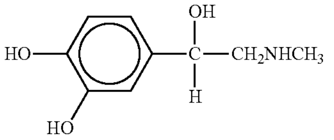

As a medication, epinephrine works by mimicking the functioning of the sympathetic nervous system, e.g., the part of the nervous system that increases heart rate, blood pressure, breathing rate and eye pupil size. More specifically, epinephrine is a non-selective alpha and beta adrenergic agonist commonly used for a variety of indications, particularly as an emergency treatment to increase mean arterial blood pressure in patients with hypotension associated with septic shock and/or other indications. In the case that anaphylaxis occurs, the patient's heart may not be able to pump sufficient quantities of blood to the rest of the human body, thus epinephrine can provide temporary relief by causing an increase in coronary blood flow. In fact, epinephrine is currently often the drug of choice in the treatment of anaphylaxis.

However, challenges exist relating to dormant storage of epinephrine formulations in typical patient care settings, such as hospitals or clinics, where epinephrine may be stored in excess 6 mo., 12 mo., or longer as needed up to a maximum storage duration of 24 months as may be in high demand in the pharmaceutical industry. Notably, maintaining the stability of epinephrine can be difficult since it is easily oxidized by reacting with oxygen while in solution or at the headspace of the container, such as a pre-filled syringe or a vial. This undesirable oxidation of epinephrine correspondingly reduces potency of the epinephrine formulation and can result in the formation of certain impurities, such as epinephrine sulfonic acid (ESA), also referred to as Impurity F. Controlling the stability of relatively low (also referred to as "junior") epinephrine concentrations such as 0.1 mg/mL, can be even more challenging than "senior" 1 mg/mL epinephrine concentrations, since even minute amounts of oxidation could jeopardize the ability of the epinephrine formulation to deliver the therapeutically effective dosage of 0.1 mg/mL epinephrine to the patient.

Further, the epinephrine formulation may also degrade over time to form its enantiomeric impurity d-epinephrine, or dextrorotary-epinephrine. In the epinephrine formulation, L-epinephrine or levorotatory-epinephrine is the far more active isomer that provides the therapeutic effects of epinephrine. However, L-epinephrine can undergo racemization over time, e.g., during dormant storage prior to administration to a patient, to form the corresponding less active d-epinephrine form. Antioxidants added to epinephrine formulations can also react with the epinephrine to form an impurity, Impurity F by the European Pharmacopeia ("EP") and British Pharmacopoeia ("BP"). In addition, degradation of epinephrine could result in discoloration of the solution.

As such, a need continues to exist for one or more epinephrine formulations, at least some of which have minimal degradants/impurities and high potency during its shelf-life.

SUMMARY

Aspects and advantages of embodiments of the present disclosure will be set forth in part in the following description, or can be learned from the description, or can be learned through practice of the embodiments.

In example embodiments, one or more formulations including epinephrine as the active pharmaceutical ingredient (API) are provided. At least some disclosed formulations have increased API retention over long-term dormant storage conditions, including up to and over 30-months. In addition, some disclosed formulations include relatively lower levels of metal-chelating agents, which decrease iron-catalyzed phenol oxidation of the formulations during storage without otherwise also undesirably decreasing zinc levels in the patient upon administration.

In one aspect, a pharmaceutical formulation includes: one or more of 0.1 mg/mL of epinephrine or a pharmaceutically acceptable salt thereof, a tonicity regulating agent including 8.2 mg/mL of sodium chloride, a pH adjusting agent including a mixture of 1.5 mg/mL sodium citrate dihydrate, 3.3 mg/mL of citric acid monohydrate, and, optionally, an as-needed amount of sodium hydroxide to maintain the pH level of the formulation within a range of 3.6 to 4.0, 0.075 mg/mL of sodium metabisulfite, and 4 μg/mL of ethylene diamine tetra-acetate disodium (EDTA). The formulation has an API recovery of 94.5% or more after at least 30 months of storage at long-term storage conditions defined as 25° C.±2° C. at 1 atmosphere (atm).

In another aspect, a pharmaceutical formulation includes: 0.1 mg/mL of an active pharmaceutical ingredient ("API"), the API comprising epinephrine or a pharmaceutically acceptable salt thereof, one or more tonicity regulating agents, one or more pH adjusting agents configured to maintain a pH level of the formulation with a range of 3.5 to 5.0, 0.01 mg/mL to about 0.08 mg/mL of sodium metabisulfite, and 1 μg/mL to 8 μg/mL of ethylene diamine tetra-acetate disodium (EDTA). The formulation is configured to result in an EDTA-zinc binding level of between about 0.19 μg/mL to about 1.6 μg/mL when administered to a human patient.

In a still further aspect, a pharmaceutical formulation includes: 1.0 mg/mL of an active pharmaceutical ingredient (API) comprising epinephrine or a pharmaceutically acceptable salt thereof, between 0.04 mg/mL and 0.08 mg/mL of an antioxidant comprising sodium metabisulfite, 6.15 mg/mL of a tonicity regulating agent, the tonicity regulating agent configured to regulate an osmolality of the formulation between 210 milliosmoles per kilogram (mOsmol/kg) and 300 mOsmol/kg, a pH-stabilizing buffer system including 2 mg/mL of citric acid and 2 mg/mL of sodium citrate configured to maintain a pH level of the formulation at 3.8, and a preservative comprising chlorobutanol. The formulation is configured to have an API recovery of greater than about 96% after storage at a storage temperature of 25° C.±2° C. for a duration of at least 24 consecutive months.

These and other features, aspects, and advantages of various embodiments of the present disclosure will become better understood with reference to the following description and appended claims. The accompanying drawings, which are incorporated in and constitute a part of this specification, illustrate example embodiments of the present disclosure and, together with the description, serve to explain the related principles.

BRIEF DESCRIPTION OF THE DRAWINGS

A full and enabling disclosure of the present disclosure, including the best mode thereof, directed to one of ordinary skill in the art, is set forth more particularly in the remainder of the specification, which makes reference to the appended drawings in which.

Figure 1:
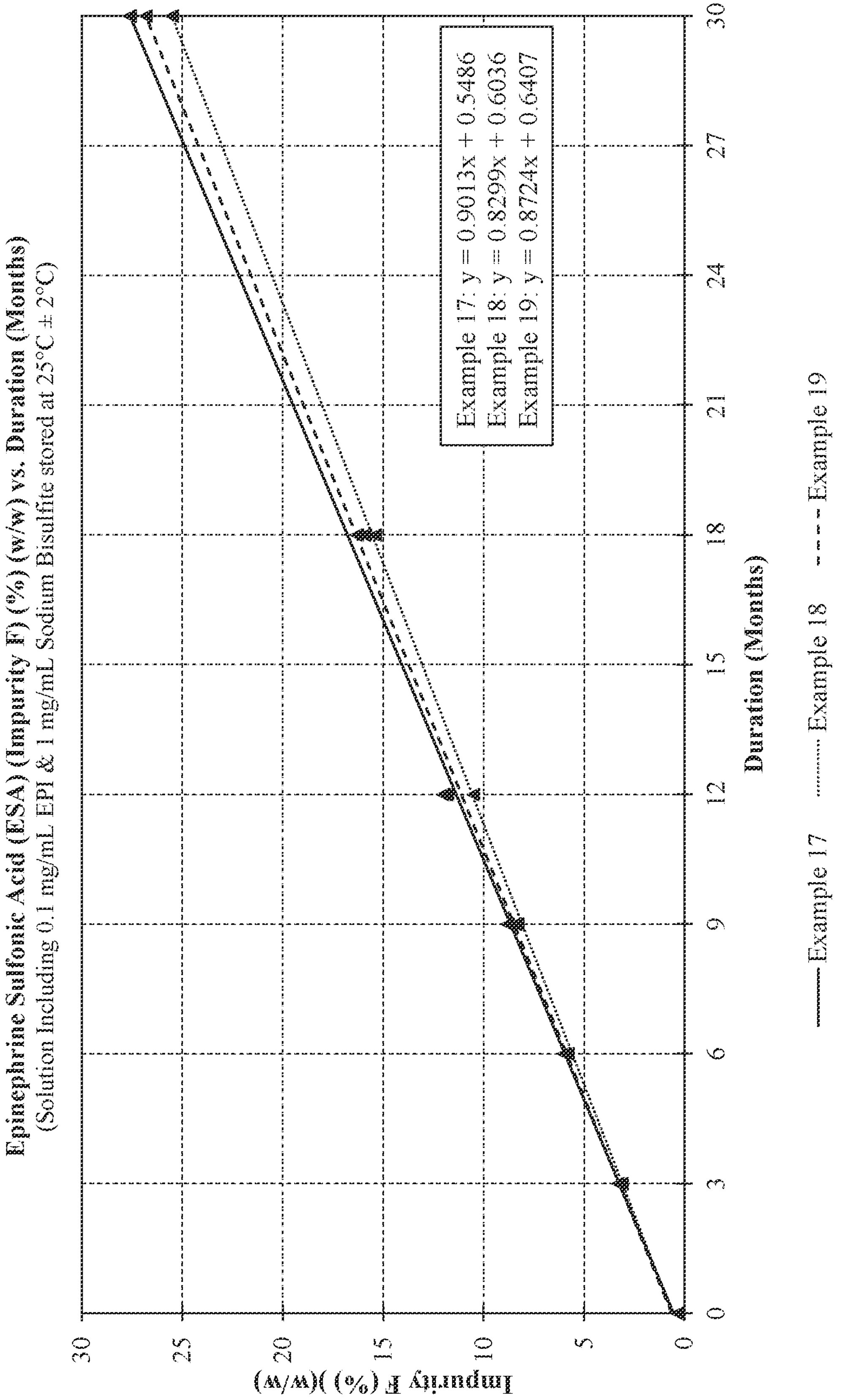
FIG. 1 depicts a graph showing the amount of Impurity F (%) (w/w) over duration (months) at a storage temperature of 25° C.±2° C. for Examples 17-19 as disclosed herein.

Repeat use of references characters in the present specification and drawing is intended to represent same or analogous features or elements of the disclosure.

DETAILED DESCRIPTION

It is to be understood by one of ordinary skill in the art that the present discussion is a description of exemplary embodiments only, and is not intended as limiting the broader aspects of the present disclosure.

Generally, the present disclosure is directed to an epinephrine formulation having low impurities and/or degradants and a relatively high potency during storage and shelf-life. Specifically, the epinephrine formulation disclosed exhibits low impurities and/or degradants and a relatively high potency for up to thirty (30) months.

The word "exemplary" is used herein to mean "serving as an example, instance, or illustration." Any embodiment described herein as "exemplary" is not necessarily to be construed as preferred or advantageous over other embodiments. Likewise, the term "embodiments" does not require that all embodiments include the discussed feature, advantage, or mode of operation.

Unless otherwise defined herein, scientific, and technical terms used in connection with embodiments of present disclosure shall have the meanings that are commonly understood by those of ordinary skill in the art. Nomenclatures used in connection with, and techniques described herein are those known and commonly used in the art. Also, descriptions of well-known functions and constructions are omitted for clarity and conciseness.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "comprising" as used herein is synonymous with "including," "containing," or "characterized by," and is inclusive or open-ended and does not exclude additional, unrecited elements or method steps; the term "having" should be interpreted as "having at least;" the term "includes" should be interpreted as "includes but is not limited to;" the term "example" is used to provide exemplary instances of the item in discussion, not an exhaustive or limiting list thereof; and use of terms like "preferably," "preferred," "desired," or "desirable," and words of similar meaning should not be understood as implying that certain features are critical, essential, or even important to the structure or function of the disclosure, but instead as merely intended to highlight alternative or additional features that may or may not be utilized in a particular embodiment of the disclosure. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition, or device includes at least the recited features or components, but may also include additional features or components. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Additionally, the phrase "consisting essentially of" will be understood to include those elements specifically recited and those additional elements that do not materially affect the basic and novel characteristics of the claimed technology. The phrase "consisting of" excludes any element not specified.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

"Treat" or "treating" or "treatment" refers to any type of action that imparts a modulating effect, which, for example, can be a beneficial effect, to a subject afflicted with a disorder, disease or illness, including preventing the manifestation of disease states associated with the condition, improvement in the condition of the subject (e.g., in one or more symptoms or in the disease), delay or reduction in the progression of the condition, and/or change in clinical parameters, disease or illness, curing the illness, etc.

The "patient" or "subject" treated as disclosed herein is, in some embodiments, a human patient, although it is to be understood that the principles of the presently disclosed subject matter indicate that the presently disclosed subject matter is effective with respect to all vertebrate species, including mammals, which are intended to be included in the terms "subject" and "patient." Suitable subjects are generally mammalian subjects. The subject matter described herein finds use in research as well as veterinary and medical applications. The term "mammal" as used herein includes, but is not limited to, humans, non-human primates, cattle, sheep, goats, pigs, horses, cats, dog, rabbits, rodents (e.g., rats or mice), monkeys, etc. Human subjects include neonates, infants, juveniles, adults, and geriatric subjects. Human subjects may have an age in years ranging from between 0 and 6, 6 and 12, 12 and 18, or over 18 (e.g., adults).

As used herein, the term "percent weight by weight" (alternatively: "% w/w", % (w/w), "weight by weight percent", or other similar language) when referring to an impurity, is the weight of the impurity divided by the weight of an API present, multiplied by 100%. For example, the percent weight by weight (or % w/w) of impurity A when 5 grams of impurity A resides in a composition having 100 grams of API B is 5% (e.g., 5 g A/(100 g API B)×100%).

As used herein, the term "weight percent" (or "wt. %" or similar language) when referring to a component, is the weight of the component divided by the weight of the composition that includes the component, multiplied by 100%. For example, the weight percent of component C when 5 grams of component C is present in 95 grams of component D is 5% (e.g., 5 g C/(5 g C+95 g D)×100%).

As used herein, the term "mole percent" (or "mole %" or similar language) when referring to a component, is the number of moles of the component divided by the total number of moles of the composition that includes the component, multiplied by 100%. For example, the mole percent of component C when 5 moles of component C is present in 95 moles of component D is 5% (e.g., 5 moles C/(5 moles C+95 moles D)×100%).

As used herein, when the term "collectively or individually" (and variations thereof) modifies an amount of a component or components (e.g., a concentration) of multiple component composition, this usage means that each individual component may be provided in the amount disclosed or that combined amount of components may be provided in the amount disclosed. For example, if agents A and B are referred to as, collectively or individually, being present in a composition at a concentration of 5 mg/mL, that means that A may be at 5 mg/mL in the composition (individually), B may be at 5 mg/mL in the composition (individually), or the combination of A and B may be present at a total of 5 mg/mL (A+B=5 mg/mL, e.g., collectively). Where A is present at 5 mg/mL, B may be absent. Where B is present at 5 mg/mL, A may be absent. Alternatively, where both A and B are present, A may be at 5 mg/mL (individually) and B may be at 5 mg/mL (individually), totaling 10 mg/mL (collectively).

When referring to a variable, the terms "or ranges including and/or spanning the aforementioned values" (and variations thereof) is meant to include any range that includes or spans the aforementioned values. For example, for the concentration of an ingredient, when the concentration of the ingredient is expressed as "1 g/ml, 5 g/ml, 10 g/ml, 20 g/ml, or ranges including and/or spanning the aforementioned values," this includes each of the particular concentrations explicitly provided or concentration ranges for the ingredient spanning any of the particular concentrations, such as, from 1 g/ml to 20 g/ml, 1 g/ml to 10 g/ml, 1 g/ml to 5 g/ml, 5 g/ml to 20 g/ml, 5 g/ml to 10 g/ml, and 10 g/ml to 20 g/ml.

As used herein, the terms "about" or "approximately" are terms of degree that avoid strict numerical boundaries. In some instances, "about" or "approximately" may be taken to mean plus or minus 10% of the numerical value those terms modify. For example, about 5% may, in some circumstances, refer to a range of values between 4.5% and 5.4%.

As used herein, any one or more of the terms "epinephrine pharmaceutical formulation," "epinephrine formulation," refers to a pharmaceutical-grade formulation having epinephrine as its API.

As used herein, the term "presently disclosed formulations" refers to the formulations described by the Examples.

As used herein, the term "EDTA" or "disodium edentate" each refers to ethylene diamine tetra-acetate disodium.

As used herein, the term "pharmaceutical formulation" refers to a formulation that includes at least one API.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. In addition, various adjuvants such as are commonly used in the art may be included. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press, which is incorporated herein by reference in its entirety. A carrier may be aqueous or may be water or saline (e.g., water, saline, saline for injection).

Commercial epinephrine formulations are available having concentrations of epinephrine ranging from 0.1 mg for so-called "junior epinephrine formulations" to 1 mg/mL for so-called "senior epinephrine formulations". However, maintaining the stability of epinephrine during long-term dormant storage conditions tends to be challenging due to epinephrine's predisposition towards oxidation by, for example, chemically reacting with oxygen in solution or in the headspace of the container, such as a pre-filled syringe or a vial. Oxidation of epinephrine in epinephrine formulations is typically undesirable, as oxidation may result in discoloration and produce undesirable impurities that correspondingly reduce the overall active pharmaceutical ingredient (API) retention over time. Moreover, controlling the stability of low epinephrine concentrations such as 0.1 mg/mL, is typically more challenging since even relatively small amounts of oxidation could still jeopardize the ability of the affected epinephrine formulation to deliver a therapeutically effective dosage (e.g., of 0.1 mg/mL) of epinephrine to the patient.

To counter the effects of epinephrine oxidation, conventional epinephrine formulations may include one or more antioxidants (e.g., sulfites or bisulfites) in various quantities. However, these antioxidants can also undesirably directly react with epinephrine within the epinephrine formulation to form an impurity, denoted as Impurity F by the European Pharmacopeia ("EP") and British Pharmacopoeia ("BP"). In some examples, Impurity F impurity may be a compound with the following chemical structure:

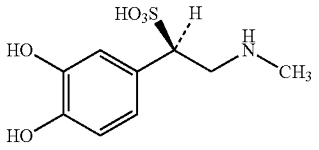 [SMILES: CNC[C@@H](c1ccc(O)c(O)c1)S(=O)(=O)O]

In some instances, the total amount of Impurity F formed in a given epinephrine formulation may be as high as 18% of the API over time, such as in the BP monograph, due to a significant amount of epinephrine degrading by either oxidation or otherwise reacting with the antioxidant to form Impurity F. Additionally, sulfite prevalent in the epinephrine formulations can cause burning or pain at the injection site, which may be unacceptable for patients.

Further, epinephrine may also degrade over time during storage and/or in relatively more acidic (e.g., pH decreased) conditions to form D-epinephrine, or dextrorotary-epinephrine, its enantiomeric impurity. D-epinephrine is considered an impurity since L-epinephrine (or levorotatory-epinephrine) is significantly more active and is thereby responsible for providing the therapeutic effects of epinephrine.

In some examples, D-Epinephrine impurity may be a compound having the following chemical structure:

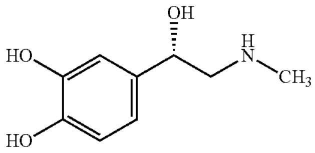

In some examples, L-epinephrine, the active isomer, may be a compound having the following chemical structure:

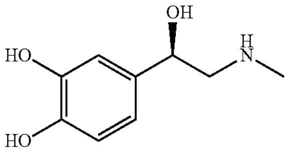

Epinephrine degrades when exposed to oxygen and may thereby degrade when exposed to the oxygen contained in ambient air. As a result, epinephrine stored in traditional storage containers, such as glass vials with rubber stoppers, can experience epinephrine degradation over time. This degradation may occur due to exposure to trace quantities of oxygen prevalent in solution (e.g., the epinephrine formulation) or at the headspace of the container. In this way, oxygen can chemically react with epinephrine contained in the epinephrine formulation to degrade the epinephrine over extended periods of dormant storage time, such as in excess of 12 consecutive months.

To proactively address such unwanted epinephrine degradation over time, epinephrine formulations can include an additional quantity of epinephrine above the minimum epinephrine concentration level required for federal regulatory approval. This additional quantity is referred to as an "epinephrine overage" and may be accounted for during initial (e.g., at a time duration of 0 months, 0 days, etc.) preparation of the epinephrine formulation. Typical epinephrine overage amounts vary, but can be as high as 15% in certain epinephrine formulations, which is the upper limit of epinephrine injection established per the USP monograph. However, inclusion of an overage amount in the epinephrine formulation can increase the risk of drug side effects or adverse reactions. Further, in some instances, administration of epinephrine formulations including an overage may result in the delivery of higher than preferred levels of epinephrine.

Further, degradation of epinephrine often results in undesirable discoloration (e.g., to a light brownish color) of the solution. As a result, metal-chelating agents (e.g., edetate disodium (EDTA), pentetic acid (DTPA), or their salts) may be occasionally included in certain epinephrine formulations to, among other things, accordingly reduce such discoloration of the epinephrine formulation. However, higher concentration levels of EDTA are unwanted due to its natural chelating properties regarding binding to other metal substances, such as zinc in the human body, or otherwise facilitating undesirable metal leaching. In addition, the most common reported undesirable side effect of EDTA is a burning sensation at the injection site. High concentration of EDTA may also cause a loss of zinc in patients [Thomas D. J., Chisolm J. Jr. Lead, zinc and copper decorporation during calcium disodium ethylenediamine tetraacetate treatment of lead-poisoned children. *J. Pharmacol. Exp. Ther.* 1986; 239(3):829-835; Apgar J. Use of EDTA to produce zinc deficiency in the pregnant rat. *J. Nutr.* 1977, 107(4):539-545. doi:10.1093/jn/107.4.539; Cossack Z T, van den Hamer C J. Evaluation of the EDTA-washed diet for use in the experimental production of zinc deficiency in human subjects. *Int. J. Vitam. Nutr. Res.* 1987; 57(1):99-102.].

Aspects of the present disclosure recognize that current epinephrine formulations may be deficient in several respects, such as (but not limited to): (1) higher than desired levels of API degradation due to oxidation of epinephrine in response to exposure to oxygen provided by ambient air during long-term storage; (2) undesirable discoloration (e.g., browning) of the epinephrine formulation in response to oxidation; (3) formation of undesirable impurities (e.g., Impurity F) due to having relatively high levels of antioxidants; (4) relatively high loading levels of metal-chelating agents (e.g., EDTA), leading to corresponding impermissible zinc loss in patients; (5) inclusion of an API overage at the time of production.

For example, presently disclosed epinephrine formulations, at a minimum, balance various components to thereby experience decreased API degradation over time relative to conventional epinephrine formulations. As a result, the presently disclosed epinephrine formulations are provided without an API overage and do not experience the side effects potentially caused by such overages. Notably, the possibility of adverse events in patients that may be caused by a higher API dosage may be significantly reduced. In addition, disclosed epinephrine formulations may also include lower amounts of antioxidants relative to other epinephrine formulations. In this way, the disclosed epinephrine formulations limit impurities generated from chemical reactions between epinephrine and the antioxidant compounds. Further, the disclosed epinephrine formulations include specific quantities of EDTA to remove metal ions (e.g., iron and zinc) and thereby reduce phenol oxidation of API and increase shelf-life stability. Notably, EDTA levels are not high enough to undesirably reduce zinc ion levels in the human body. This reduction can otherwise occur due to metal binding between a metal-chelating agent (e.g., EDTA) and zinc in the patient upon administration of the epinephrine formulation. In this way, the disclosed epinephrine formulations also reduce the possibility of undesirable zinc deficiency in patients. In addition, disclosed epinephrine formulations resist pH changes and maintain a desired pH range during its shelf life.

I. Active Pharmaceutical Ingredient (API)

The presently disclosed epinephrine formulations include epinephrine as the API. As used herein "epinephrine" refers to epinephrine or a pharmaceutically acceptable salt thereof. Examples of pharmaceutically acceptable salts of epinephrine include, for example, acetate, bitartrate, carbonate, citrate, hydrochloride, hydrocyanide, hydrofluoride, nitrate, nitrite, phosphate, and sulfate salts. As used, "epinephrine" refers to L-epinephrine, also commonly known as levorotatory-epinephrine, the relatively more active isomer that is responsible for providing the therapeutic effects of epinephrine. By contrast, D-epinephrine, or dextrorotatory-epinephrine, is significantly less active than the L-epinephrine and may be considered as a type of impurity. As a result, the potency of epinephrine API is driven by the significantly more active L-epinephrine. In addition, as presented in one or more Examples provided herein API % recovery per label claim or % API recovery relative to API measured at 0 mo. (e.g., 100% at 0 mo.) at Room Temperature, refers to L-epinephrine recovery. As L-epinephrine degrades over time, it may form D-epinephrine. In several embodiments, the epinephrine is L-epinephrine, or a pharmaceutically acceptable salt thereof. In the present disclosure, references to epinephrine may relate to either of: (1) substantially enantiomerically pure L-epinephrine; or, in the alternative, (2) a combination of both L-epinephrine and D-epinephrine.

The presently disclosed epinephrine formulations can include epinephrine at various defined concentration levels to meet specific therapeutic needs, e.g., in both low-dosage or "junior" (e.g., 0.1 mg/mL) as well as non-low dosage or "senior" (1 mg/mL) types. In addition, or the alternative, the presently disclosed epinephrine formulations can include epinephrine in ranges extending from about 0.05 mg/mL to about 1.5 mg/mL, such as from about 0.1 mg/mL to about 1 mg/mL, such as from about 0.5 mg/mL to about 0.7 mg/mL. In other embodiments, the concentration of epinephrine can be equal to or less than about: concentration of equal to or less than about: 0.05 mg/mL, 0.075 mg/mL, 0.09 mg/mL, 0.10 mg/mL, 0.11 mg/mL, 0.12 mg/mL, 0.13 mg/mL, 0.14 mg/mL, 0.15 mg/mL, 0.20 mg/mL, or ranges including and/or spanning the aforementioned values. Any one or more of the presently disclosed epinephrine concentrations can be provided without an overage.

II. Antioxidants

The epinephrine formulations can also be prepared to include one or more antioxidants, e.g., referring to substances that inhibit oxidation, especially those used to counteract the deterioration of stored drug products. The antioxidant can include, for example, sodium metabisulfite, sodium bisulfite, potassium metabisulfite, d-ascorbic acid, thioglycerol, N-acetyl-cysteine, L-ascorbic acid, other sulfites, butylated hydroxytoluene, and/or tocopherol, and/or other suitable antioxidants and is not limited to the presented examples. The epinephrine formulation may include an antioxidant at a concentration ranging from about 0.01 mg/mL to about 0.1 mg/mL, such as from about 0.05 mg/mL to about 0.08 mg/mL. In certain embodiments, the epinephrine formulation includes antioxidant at a concentration of less than about 0.1 mg/mL. In an embodiment, the epinephrine formulation comprises 0.075 mg/mL of antioxidant(s). In other embodiments, the epinephrine formulation comprises from about 0.02 mg/mL to about 1 mg/mL, such as from about 0.04 mg/mL to about 0.08 mg/mL. In a certain embodiment, the epinephrine formulation comprises sodium metabisulfite at a concentration of about 0.075 mg/mL. In yet another embodiment, the epinephrine formulation comprises sodium metabisulfite at a concentration of from about 0.04 mg/mL to about 0.08 mg/mL.

III. Metal Chelating Agent

The epinephrine formulation may include one or more metal chelating agent(s), e.g., referring to substances facilitating the bonding of ions and molecules to metal ions. Specifically, chelation refers to the formation or presence of two or more separate coordinate bonds between a polydentate ligand and a single central metal atom. Suitable metal chelating agents can include ethylene diamine tetra-acetate disodium (EDTA), pentetic acids (DTPA), and their salts. In several examples, the epinephrine formulations include one or more metal chelating agents at a concentration ranging from 1 μg/mL to 200 μg/mL, such as 5 μg/mL to about 150 μg/mL, such as from about 20 μg/mL to about 100 μg/mL. In one embodiment, the epinephrine formulation includes from about 1 μg/mL to about 8 μg/mL, such as from about 2 μg/mL to about 7 μg/mL, such as about 3 μg/mL to about 6 μg/mL, such as about 4 μg/mL to about 5 μg/mL. In one embodiment, the epinephrine formulation includes 4 μg/mL. In some examples, the metal chelating agent comprises, consists of, or consists essentially of ethylene diamine tetra-acetate disodium ("EDTA"). In other embodiments, the epinephrine formulations may be substantially free from metal chelating agents.

IV. Tonicity Regulating Agent(s)

The composition herein may include one or more tonicity regulating agent(s), e.g., referring to substances designed to reduce local irritation by preventing osmotic shock at the site of application. Suitable tonicity regulating agents can include sodium chloride, dextrose, glucose, glycerin, cellulose, mannitol, polysorbate, propylene glycol, sodium iodide, and combinations thereof. Further, the epinephrine formulation may include any pharmaceutically acceptable tonicity regulating agent. The tonicity regulating agent may be present at a concentration sufficient to regulate an osmolality of the epinephrine formulation to be equal to or less than about: 290 mOsmol/Kg, 293 mOsmol/Kg, 296 mOsmol/Kg, 300 mOsmol/Kg, 301 mOsmol/Kg, 302 mOsmol/Kg, 303 mOsmol/Kg, 304 mOsmol/Kg, 306 mOsmol/Kg, 308 mOsmol/Kg, 310 mOsmol/Kg, or ranges including and/or spanning the aforementioned values. For example, in several embodiments, the epinephrine formulation may comprise a tonicity agent (or combination of tonicity agents) at or below a concentration sufficient to regulate an osmolality at any of the aforementioned values. Additionally, as further illustrated, the epinephrine formulation may comprise the tonicity agent(s) at a concentration sufficient to regulate an osmolality of the epinephrine formulation to have a value ranging between, for example, 290 mOsmol/Kg to 310 mOsmol/Kg, 295 mOsmol/Kg to 305 mOsmol/Kg, 300 mOsmol/Kg to 305 mOsmol/Kg, etc. In some embodiments of the epinephrine formulations, the tonicity agent regulates an osmolality of the epinephrine formulation to be 290 mOsmol/Kg to 310 mOsmol/Kg, including any osmolality subsumed therein, including but not limited to 295 mOsmol/Kg to 305 mOsmol/Kg, or 300 mOsmol/Kg to 305 mOsmol/Kg. In further embodiments of the epinephrine formulations, the tonicity agent regulates an osmolality of the epinephrine formulation to be about 300 mOsmol/Kg, about 301 mOsmol/Kg, about 302 mOsmol/Kg, about 303 mOsmol/Kg, about 304 mOsmol/Kg, about 305 mOsmol/Kg, about 306 mOsmol/Kg, about 307 mOsmol/Kg, about 308 mOsmol/Kg, about 309 mOsmol/Kg, or about 310 mOsmol/Kg.

The epinephrine formulation can include one or more tonicity regulating agents at a concentration ranging between 1.0 mg/mL and 10.0 mg/mL, 3.0 mg/mL and 10.0 mg/mL, 5.0 mg/mL to 9.0 mg/mL, etc. In certain embodiments, the tonicity regulating agent is present at a concentration 1.0 mg/mL to 10.0 mg/mL, or any concentration subsumed therein, including but not limited to, 3.0 mg/mL to 10.0 mg/mL, 3.0 mg/mL to 9.0 mg/mL, 5.0 mg/mL to 10.0 mg/mL, or 5.0 mg/mL to 9.0 mg/mL. In other certain embodiments, the epinephrine formulation includes sodium chloride as the tonicity regulating agent and the sodium chloride is present at a concentration of about 1.0 mg/mL, about 2.0 mg/mL, about 3.0 mg/mL, about 4.0 mg/mL, about 5.0 mg/mL, about 6.0 mg/mL, about 7.0 mg/mL, about 7.5 mg/mL, about 8.0 mg/mL, 8.2 mg/mL, about 8.5 mg/mL, about 9.0 mg/mL, about 9.5 mg/mL, or about 10.0 mg/mL. In an embodiment, the tonicity regulating agent includes sodium chloride and the sodium chloride is present at a concentration of about 5 mg/mL to about 7 mg/mL. In embodiments, the tonicity agent comprises, consists of, or consists essentially of sodium chloride.

V. pH Buffers

The epinephrine formulation can include one or more buffers, such as on one or more pH buffers capable of maintaining a desired pH for the epinephrine formulation. Suitable buffers can include citric acid, sodium citrate, sodium phosphate, or a combination thereof. The buffer functions to provide a total acidity of the epinephrine formulation of not more than 0.05 equivalent. In some embodiments, the buffer includes a buffer pair having a first buffer and a second buffer. In the buffer pair, the total acidity of the epinephrine formulation of not more than 0.05 equivalent is maintained by the interaction between an acid, such as a weak acid, and its conjugate base. In some embodiments of the buffer pair, the first buffer is citric acid, and the second buffer is sodium citrate. The citric acid can be citric acid monohydrate. The sodium citrate can be sodium citrate dihydrate.

The buffer system can include an acid and its conjugate base. In embodiments, the buffer can include a first buffer agent (e.g., an acid), such as citric acid, and a second buffer agent (e.g., a conjugate base), such as sodium citrate, thereby forming a buffer pair. In some embodiments, the acid (e.g., conjugate acid) is adipic acid, ammonium chloride, citric acid, acetic acid, formic acid, lactic acid, phosphoric acid, propionic acid, tartaric acid, combinations of the foregoing, or other acids. In several embodiments, the base (e.g., conjugate base) is acetate (e.g., sodium acetate, etc.), citrate (e.g., sodium citrate, etc.), bicarbonate (e.g., sodium bicarbonate, etc.), carbonate (e.g., sodium carbonate), lactate (e.g., sodium lactate, etc.), phosphate (e.g., sodium phosphate), combinations of the foregoing, or other bases. In embodiments, the buffer can be a phosphate buffer, an acetate buffer, or a citrate buffer. In another embodiment, the buffer is a citrate buffer. In yet another embodiment, the buffer is a 2-ethanesulfonic acid (MES) hydrate or monohydrate buffer. In still another embodiment, the buffer is a bis-tris methane (BIS TRIS) buffer.

In some embodiments, the epinephrine formulations comprise of the first buffer, citric acid, at a concentration ranging from 1.6 mg/mL to 6.0 mg/mL. The epinephrine formulation comprises of the second buffer, sodium citrate, at a concentration ranging from 0.4 mg/mL to 6 mg/mL.

In some embodiments, the epinephrine formulation further includes a pH adjustor and/or one or more pH adjustor. In embodiments, the pH adjustor(s) includes one or more of hydrochloric acid (HCl), sodium hydroxide (NaOH), acetic acid, ascorbic acid, sulfuric acid, tartaric acid, or a combination thereof. In another embodiment, the pH adjustor includes 10% (w/v) HCl and as needed or desired, NaOH.

The epinephrine formulations can have a pH ranging from about 3 to about 5, such as from about 3.6 to about 4.0.

In certain embodiments, the pharmaceutical formulation does not include tartrate or its acids (e.g., tartaric acid), bases, or salts, thereof. For instance, the pharmaceutical formulation may be substantially free from tartrate and its acids, bases, or salts, thereof. In such embodiments, a pharmaceutical formulation is provided that is substantially free from tartrate and its acids, bases, or salts and also includes a very low amount of metal chelating agent (e.g., EDTA), which is capable of reducing impurities/degradants of the pharmaceutical formulation during shelf-life. As discovered by the inventors of the present disclosure, such a reduced amount of metal chelating agent without the addition of other chelating agents or tartrate its acids, bases, or salts, was sufficient for reducing impurities and degradation of the pharmaceutical formulation for time periods of at least twelve (12) months, such as at least eighteen (18) months, such as at least twenty-four (24) months, such as up to an estimated thirty (30) months.

VI. Dosage Forms

The epinephrine formulations of the present disclosure can be administered to a patient by parenteral administration, such as via intramuscular ("IM"), subcutaneous ("SC"), or intravenous ("IV") injections. In situations where the pharmaceutical formulation is used as an emergency treatment, parenteral administration is preferred over other routes of administration, such as oral administration, due to faster absorption rates observed in parenteral administration. In an IV administration, the epinephrine pharmaceutical formulation may be diluted, and the diluted formulation can be injected or infused slowly by IV into a patient. Close monitoring of epinephrine administration is recommended, because an inadvertent overdose of epinephrine can be fatal, cause moderate to severe undesirable effects, and/or be toxic (i.e., hypertension).

In some embodiments, the pharmaceutical formulation is prepared as an aqueous solution, e.g., referring to a solution in which the solvent is water. In addition, the epinephrine formulation may be contained in a pre-filled syringe having a total volume of 1 mL to 10 mL. In other embodiments, the pharmaceutical formulation is contained in a vial having a total volume of 1 mL to 10 mL. In still other embodiments, the pharmaceutical formulation is contained in any type of pharmaceutically acceptable container having a total volume of 1 mL to 10 mL. For example, total epinephrine content per container (e.g., pre-filled syringe, vial, etc.) in "junior" formulations prepared with a concentration level of 0.1 mg/mL epinephrine provided without an overage may be calculated as follows: 0.1 mg/mL (concentration level)×10 mL (container)=1 mg. Likewise, total epinephrine content in "senior" formulations prepared with a concentration level of 1 mg/mL epinephrine provided without an overage may be calculated as follows: 1 mg/mL (concentration level)×10 mL (container)=10 mg.

Several presently disclosed embodiments relate to dispensing devices for administering the compositions disclosed herein. For example, the pharmaceutical compositions may be provided in a dispenser device accompanied by instructions for administration (e.g., as a kit). In addition, the dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration (FDA) for prescription drugs, or the approved product insert. Compositions that can include epinephrine and/or salts thereof may be placed in an appropriate container and/or dispensing device, and labeled for treatment of an indicated condition.

In several embodiments, the dispensing device comprises a vessel. The term "vessel" is used herein in accordance with its ordinary meaning in the art and includes any structure and/or device which is capable of holding an epinephrine composition in fluid communication with a dispensing component. A dispensing component may be any feature which is capable of fluid communication with a vessel and dispensing an epinephrine composition to a variety of human patients and/or animal patients. Examples may include, but are not limited to, needles, etc. These devices may be further packaged in a film or other sealing material that may be configured to easily be removed prior to use of the device.

In several embodiments, the vessel may comprise a cylinder and may contain an aqueous pharmaceutical formulation of the present disclosure. The vessel may be connected to a dispensing component. In addition, the dispensing device may comprise an actuator (a trigger, button, plunger, etc.) that may be actuated to dispense the pharmaceutical formulation. Still further, the dispensing device may be configured to distribute a liquid pharmaceutical formulation into the patient.

VII. Method of Treating

The disclosed epinephrine formulations can provide rapid delivery of epinephrine to a human patient to, for example, treat certain indications by, for example, increasing mean arterial blood pressure in adult patients with hypotension associated with septic shock. In several embodiments, the delivery is comparable to 1 mg/mL epinephrine IM auto-injectors. Accordingly, disclosed are methods of providing a rapid delivery of epinephrine to, for example, an adult human patient, the method comprising the step of administrating a dose amount of epinephrine from any of the disclosed epinephrine formulations. Multiple techniques of administering a pharmaceutical formulation as disclosed herein exist including, but not limited to, injection and parenteral delivery, including intramuscular, subcutaneous, intravenous, direct intraventricular, and intraperitoneal injections.

In several embodiments, as disclosed herein, methods of treating a condition are provided, e.g., including identifying a human patient in need of treatment due to suffering from a condition or being at risk of suffering from a condition as disclosed elsewhere herein. In several embodiments, the method comprises administering a dose of a formulation as described herein to the patient to treat and/or cure the patient as a result of receiving the dose.

VIII. Impurities/Degradants

As further explained in the examples provided herein, disclosed epinephrine formulations may be prepared so as to form lower amounts of impurities and/or degradants as a result of long-term dormant storage relative to conventional commercially-available pharmaceutical grade epinephrine formulations. That is, ingredients used in the presented formulations may collectively function to unexpectedly and favorably decrease overall impurity and/or degradant production over time, thereby permitting for relatively long storage durations, such as 18-months, or 30-months or longer.

For example, certain embodiments of at least some of the presently disclosed epinephrine formulations described by, for example, at least Examples 1-3 (e.g., as shown in Table 1 below) have an initial concentration of 0.1 mg/mL of epinephrine provided without an overage. The disclosed formulations described by Examples 1-3 generally include enantiomeric impurity D-epinephrine in an amount of not more than ("NMT") 3.2% w/w, NMT 3.9% w/w of Impurity F, and/or NMT 4.5% w/w of total related impurities excluding D-epinephrine after storage at a temperature of 40° C. for a period of three (3) months (denoted as "3M" in Table 1). In some embodiments, the disclosed formulations have an API recovery (e.g., an L-epinephrine recovery) of at least 94.9% after storage at a temperature of 40° C. for a period of three (3) months.

In some embodiments, at least some of the disclosed formulations described by, for example, Examples 1-3 (e.g., as shown in Table 1 below) generally have an initial concentration of 0.1 mg/mL epinephrine provided without an overage including NMT 1.6% w/w D-epinephrine, NMT 2.8% w/w Impurity F, NMT 3.4% w/w of total related impurities (excluding D-epinephrine) after storage at temperature of about 25° C. (denoted as room temperature, "RT" in Table 1) for eighteen (18) months. In some embodiments, the epinephrine formulations have an API recovery (e.g., an L-epinephrine recovery) of at least 96.8% after storage at a temperature of 25° C. for a period of eighteen (18) months.

In some embodiments, at least some of the disclosed formulations described by, for example, Examples 5-8 (e.g., as shown in Table 2 below) generally have an initial concentration of 0.1 mg/mL epinephrine provided without an overage including NMT 2.7% w/w D-epinephrine after storage at temperature of about 40° C. for three (3) months. In embodiments, the epinephrine formulations have an API recovery (e.g., an L-epinephrine recovery) of at least 94.8% after storage at a temperature of 40° C. for a period of three (3) months.

In some embodiments, at least some of the disclosed formulations described by, for example, Examples 5-8 (e.g., as shown in Table 2 below) generally have an initial concentration of 0.1 mg/mL epinephrine provided without an overage that generally includes NMT 1.8% w/w D-epinephrine, NMT 3.7% w/w Impurity F, and/or NMT 4.1% w/w of total related impurities (excluding D-epinephrine) after storage at temperature of about 25° C. (denoted as room temperature, "RT" in Table 2) for a storage period of twenty-four (24) months. In embodiments, the epinephrine formulations have an API recovery (e.g., an L-epinephrine recovery) of at least 96.3% after storage at a temperature of 25° C. for a period of twenty-four (24) months.

In some embodiments, the disclosed formulations described by, for example, Examples 11-13 (e.g., as shown in Table 3 below) generally have an initial concentration of 0.1 mg/mL of epinephrine provided without an overage including NMT 3.6% w/w D-epinephrine, NMT 3.8% w/w Impurity F, and/or NMT 4.6% of total related impurities (excluding D-epinephrine) after storage at temperature of 40° C. for a storage period of three (3) months. In some embodiments, the formulations have an API recovery (e.g., an L-epinephrine recovery) of at least 98.3% after storage at a temperature of 40° C. for a storage period of three (3) months.

In some embodiments, the disclosed formulations described by, for example, Examples 11-13 (e.g., as shown in Table 3 below) generally have an initial concentration of 0.1 mg/mL of epinephrine provided without an overage including NMT 7.3% w/w D-epinephrine, NMT 5.5% w/w Impurity F, and/or NMT 7.1% of total related impurities (excluding D-epinephrine) after storage at temperature of 40° C. for a storage period of six (6) months. In some embodiments, the formulations have an API recovery (e.g., an L-epinephrine recovery) of at least 96.9% after storage at a temperature of 40° C. for a storage period of six (6) months.

In some embodiments, the disclosed formulations described by, for example, Examples 11-13 (e.g., as shown in Table 3 below) generally have an API recovery (e.g., an L-epinephrine recovery) of at least 99.3% after storage at a temperature of 25° C. (denoted as room temperature, "RT" in Table 3) for a period of fifteen (15) months and an API recovery (e.g., an L-epinephrine recovery) of 97.9% after storage at a temperature of 25° C. (denoted as room temperature, "RT" in Table 3) for a period of twenty-four (24) months.

In some embodiments, the disclosed formulations described by, for example, Examples 20-22 (e.g., as shown in Table 5 below) generally have an initial concentration of 0.1 mg/mL of epinephrine provided without an overage including NMT 3.3% w/w D-epinephrine, NMT 5.4% w/w Impurity F, and/or NMT 6.4% total related impurities (excluding D-epinephrine) after storage at temperature of about 30° C. for a storage period of twelve (12) months. In embodiments, the epinephrine formulations have an API recovery (e.g., an L-epinephrine recovery) of at least 95.7% after storage at a temperature of 30° C. for a period of twelve (12) months.

In some embodiments, the disclosed formulations described by, for example, Examples 20-22 (e.g., as shown in Table 5 below) generally have an initial concentration of 0.1 mg/mL of epinephrine provided without an overage including NMT 5.6% w/w D-epinephrine, NMT 8.6% w/w Impurity F, and/or NMT 10.4% total related impurities (excluding D-epinephrine) after storage at a temperature of about 40° C. for a storage period of six (6) months. In embodiments, the epinephrine formulations have an API recovery (e.g., an L-epinephrine recovery) of at least about 93.9% after storage at a temperature of 40° C. for a storage period of six (6) months.

In some embodiments, the disclosed formulations described by, for example, Examples 20-22 (e.g., as shown in Table 5 below) generally have an initial concentration of 0.1 mg/mL of epinephrine provided without an overage including NMT 2.2% w/w D-epinephrine, NMT 4.6% w/w Impurity F, and/or NMT 5.4% total related impurities (excluding D-epinephrine) after storage at temperature of about 25° C. (denoted as room temperature, "RT" in Table 5) for a storage period of eighteen (18) months. In embodiments, the epinephrine formulations have an API recovery (e.g., an L-epinephrine recovery) of at least 96.9% after storage at a temperature of 25° C. for a period of eighteen (18) months.

In some embodiments, the disclosed formulations described by, for example, Examples 30-31 (e.g., as shown in Table 7 below) generally have an initial concentration of 1 mg/mL of epinephrine provided without an overage including NMT 5.3% w/w D-epinephrine after storage at a temperature of about 40° C. for a storage period of six (6) months. In some embodiments, the epinephrine formulations have an API recovery (e.g., an L-epinephrine recovery) of at least about 90.3% after storage at a temperature of 40° C. for a storage period of six (6) months.

In some embodiments, the disclosed formulations described by, for example, Examples 30-31 (e.g., as shown in Table 7 below) generally have an initial concentration of 1 mg/mL of epinephrine provided without an overage including NMT 0.81% w/w D-epinephrine after storage at a temperature of about 25° C. (denoted as room temperature, RT, in Table 7) for a storage period of six (6) months. In some embodiments, the epinephrine formulations have an API recovery (e.g., an L-epinephrine recovery) of at least about 98.5% after storage at a temperature of 25° C. for a storage period of six (6) months.

In some embodiments, the disclosed formulations described by, for example, Examples 30-31 (e.g., as shown in Table 7 below) generally have an initial concentration of 1 mg/mL of epinephrine provided without an overage including NMT 2.06% w/w D-epinephrine after storage at a temperature of about 25° C. (denoted as room temperature, RT, in Table 7) for a storage period of twenty-four (24) months. In some embodiments, the epinephrine formulations have an API recovery (e.g., an L-epinephrine recovery)

of at least about 96.6% after storage at a temperature of 25° C. for a storage period of twenty-four (24) months.

EXAMPLES

As disclosed in the Examples herein, the impurities and/or degradants of the presently disclosed formulations are determined by storing the epinephrine formulations over a defined period of time, and at a desired temperature to test for impurities under such conditions. In at least some of the presently disclosed examples, the epinephrine formulations are stored at a storage temperature ranging between 20° C. to 60° C. In some examples, storage conditions include a storage temperature of equal to or at least about 25° C. (or room temperature) and 40° C. Storage conditions may also include a storage period of, for example, equal to or at least: 1 week, 2 weeks, 3 weeks, 4 weeks, 1 month, 3 months, 6 months, 12 months, 18 months, 24 months or longer, or ranges contained within, including and/or spanning the aforementioned values. Additionally, the API and impurities (i.e., Impurity F, D-Epi, and Total Related Impurities excluding D-Epi) concentrations can be tested at time zero, which is the time point the formulation passes the drug release specification at the time of batch release.

The determination of impurities after set time intervals in various storage temperature condition or "stability" of the presented epinephrine formulations evaluated the overall concentration of impurities. The stability study was performed in reference to ICH Harmonised Tripartite Guideline: Stability Testing of New Drug Substances and Product Q1A (R2), dated 6 Feb. 2003. In some examples, stability impurities tests for the long term, intermediate, and/or accelerated were measured by using validated reversed phase high-performance liquid chromatography (HPLC) after storage in the following conditions, wherein the formulations are packaged in a container closure system, glass vial sealed with an elastomeric stopper. In some examples, impurities test was performed between "time zero" and the minimum time period covered as depicted in the provided examples.

| Study | Storage condition | Minimum Time Period Covered |
|---|---|---|
| Long Term | 25° C. ± 2° C./ Ambient Humidity | 24 months |
| Intermediate | 30° C. ± 2° C./ Ambient Humidity | 12 months |
| Accelerated | 40° C. ± 2° C./ Ambient Humidity | 6 months |

In several examples, storage conditions may include conditions as provided in the examples and may be performed on formulations that are stored in a nitrogen atmosphere. The storage time, storage temperature, storage humidity, storage container, and any combination of the aforementioned conditions may be varied. In several examples, the epinephrine formulations are stored in a glass container with elastomeric closure.

Tests for the API potency and the aforementioned impurities (i.e., Impurity F, D-Epi, Total related impurities excluding D-Epi) were all conducted using several validated HPLC methods:

The general potency or assay HPLC method was performed as referenced in the *USP* 43 *NF* 38 *Epinephrine Injection monograph.*

The enantiomeric impurity test procedure for D-Epi was performed as referenced in the *USP PF* 43(3) using a Shodex Chiral LC column.

To detect and quantify the Impurity F and total related impurities, an HPLC method was derived and modified from the *European Pharmacopeia* ("EP") 10.7 *Adrenaline monograph Related Substances* (*Ph. Eur. Monograph*). The modified EP, in-house method improved resolution of known impurities (i.e., Impurity F) as well as evaluating other known impurities not listed in any compendia references. The HPLC conditions for testing related impurities is described below:

| HPLC Condition for Impurity F and Total related impurities | |
|---|---|
| Solvent Mixture A | 5 g/mL potassium dihydrogen phosphate, 2.6 g/mL sodium octanesulfonate, adjust pH 2.8 |
| Solvent Mixture C | 2.5 g/mL potassium dihydrogen phosphate, 1.2 g/mL sodium octanesulfonate, adjust pH 4 |
| Column | Stationary phase: end-capped octadecylsilyl silica gel<br>Size: 4.6 mm × 100 mm<br>Temperature: 50° C. |
| Flow Rate | 2 mL/min |
| Wavelength | 210 nm (UV) |
| Injection volume | 20 μl |
| Mobile Phase A | ACN, Solvent Mixture A |
| Mobile Phase B | ACN, Solvent Mixture A |

Gradient Program

| Time (min) | Solvent Mixture C | Mobile Phase A | Mobile Phase B |
|---|---|---|---|
| 0-2 | 100 | 0 | 0 |
| 2-2.1 | 100→0 | 0→92 | 0→8 |
| 2.1-17 | 0 | 92 → 50 | 8 → 50 |
| 17-22 | 0 | 50 → 92 | 50 → 8 |
| 22-27 | 0 | 92 | 8 |
| 27-27.1 | 0→100 | 92→0 | 8→0 |
| 27.1-37 | 100 | 0 | 0 |

(1) API recovery %, (2) enantiomeric impurity, (3a) impurity F, and (3b) total related impurities are determined using 3 separate/individual test methods as described below:

| # | Item | Test Method | Reference |
|---|---|---|---|
| 1 | API recovery % | Assay, HPLC | Epinephrine Injection USP 43 NF 38 |
| 2 | Enantiomeric (D-Epi) impurity | Enantiomeric Purity | Epinephrine Injection USP PF 43(3) |
| 3a | Epinephrine Sulfonic Acid (ESA) (Impurity F) | Related Substances | |
| 3b | Total Related Impurities | | In-house method (Modified from EP 10.7 Adrenaline monograph Related Substances) |

As indicated in the Examples provided below, API recovery % is the API (or epinephrine) amount as a percent of label claim or indicated relative to API measured at 0 mo. at Room Temperature. That is, API recovery is relative to initial API measured at 0 mo. at Room Temperature, such as 100.0%. In some instances, the initial API measured may not include all impurities present in the formulation at that time due to, for example, potential detection variances.

Examples 1-4: Effectiveness of EDTA on Epinephrine Formulations

The effectiveness of disodium edetate (EDTA), a type of metal-chelating agent, on reducing the impurities of epinephrine formulations was studied on Examples 1-4, as shown in Table 1 below. This study was conducted on each of Examples 1-4 with the following storage conditions: 3-months (40° Celsius), 6-months (RT), 12-months (RT), 15-months (RT), and 18-months (RT).

For Examples 1-4 in Table 1, each epinephrine formulation included L-Epinephrine as the API, sodium metabisulfite as the antioxidant, EDTA as the metal-chelate agent, sodium chloride as the tonicity agent, sodium citrate dihydrate and citric acid monohydrate as the buffer agents, and had a pH of 3.8. Example 1 was prepared under an atmosphere of nitrogen to provide an aqueous solution of L-Epinephrine (0.1 mg/ml), sodium chloride (5.5 mg/ml), sodium citrate dihydrate (6 mg/ml), citric acid monohydrate (6 mg/ml), EDTA (8 μg/ml), and sodium metabisulfite (0.08 mg/ml), and the pH of the aqueous solution was adjusted to pH 3.8 using hydrochloric acid (HCl) and sodium hydroxide (NaOH). The aqueous solution was filtered through a 0.22 μm filter and the resultant solution was filled into a glass vial container having a 13 mm rubber closure under nitrogen protection. Examples 2-4 were prepared in a manner similar to that described with respect to Example 1 except for using different concentrations of EDTA (4, 2, and 0 μg/ml, respectively). Example 4, which did not include EDTA, serves as the Control.

"Total related impurities" is defined as the sum of specified impurities (e.g., Impurity F) and unspecified impurities collectively excluding D-epinephrine. Impurities were quantified via an external standard against a standard solution containing main component (epinephrine). For example, total related impurities may include sulfated epinephrine, hydroxylated epinephrine, unspecified impurities (that are too minimal to characterize or that have not been characterized), etc.

TABLE 1

Effectiveness of EDTA on the Epinephrine Formulations for Examples 1-4.

Epinephrine Formulations for Examples 1-4

| | Ingredient | | Example # 1 | 2 | 3 | 4 |
|---|---|---|---|---|---|---|
| 1 | API | L-Epinephrine, mg/mL | 0.1 | 0.1 | 0.1 | 0.1 |
| 2 | Antioxidant | Sodium metabisulfite, mg/mL | 0.08 | 0.08 | 0.08 | 0.08 |
| 3 | Metal-chelator | Disodium Edetate (EDTA), μg/mL | 8 | 4 | 2 | 0 |
| 4 | Tonicity | Sodium Chloride, mg/mL | 5.5 | 5.5 | 5.5 | 5.5 |
| 5 | buffer agent | Sodium citrate dihydrate, mg/mL | 6 | 6 | 6 | 6 |
| 6 | buffer agent | Citric acid monohydrate, mg/mL | 6 | 6 | 6 | 6 |
| | pH | pH Unit | 3.8 | 3.8 | 3.8 | 3.8 |
| | Compounding Overage | | 0% | 0% | 0% | 0% |
| | API recovery, % (relative to API measured at 0 mo. at Room Temperature) | | | | | |
| | 40° C. 3 M | | 95.1% | 94.9% | 95.1% | 92.1% |
| | RT 6 M | | 98.5% | 98.5% | 98.4% | 98.0% |
| | RT 12 M | | 98.0% | 97.9% | 97.8% | 96.8% |
| | RT 15 M | | 97.3% | 97.4% | 97.2% | 96.0% |
| | RT 18 M | | 97.0% | 96.8% | 96.8% | 95.5% |
| | Enantiomeric Impurity: D-Epinephrine (D-Epi) | | | | | |
| | 40° C. 3 M | | 3.1% | 3.2% | 3.1% | 3.2% |
| | RT 6 M | | 1.0% | 1.0% | 1.0% | 1.1% |
| | RT 12 M | | 1.1% | 1.1% | 1.1% | 1.1% |
| | RT 15 M | | 1.6% | 1.5% | 1.6% | 1.5% |
| | RT 18 M | | 1.6% | 1.6% | 1.6% | 1.7% |
| | Epinephrine Sulfonic Acid (Impurity F) (w/w) | | | | | |
| | 40° C. 3 M | | 3.9% | 3.9% | 3.9% | 5.2% |
| | RT 6 M | | 1.3% | 1.4% | 1.4% | 1.3% |
| | RT 12 M | | 2.0% | 2.2% | 2.1% | 2.4% |
| | RT 15 M | | 2.7% | 2.8% | 2.7% | 2.8% |
| | RT 18 M | | 2.6% | 2.7% | 2.8% | 5.1% |
| | Total Related Impurities (Excluding D-Epi) (w/w) | | | | | |
| | 40° C. 3 M | | 4.3% | 4.3% | 4.5% | 6.2% |
| | RT 6 M | | 1.7% | 1.8% | 1.8% | 3.0% |
| | RT 12 M | | 2.7% | 2.8% | 2.9% | 6.0% |
| | RT 15 M | | 3.3% | 3.3% | 3.3% | 6.7% |
| | RT 18 M | | 3.2% | 3.2% | 3.4% | 7.4% |

Advantageously, the impurity results in Table 1 demonstrate that low amounts of metal-chelate agent, such as 2-8 μg/ml EDTA, is effective in reducing impurities for Examples 1-3. As used herein Room Temperature ("RT") refers to a temperature of at or about 25° C. In particular, as demonstrated in Table 1, Examples 1-3 exhibited:

a. Enantiomeric Impurity, D-Epinephrine (D-Epi) of NMT 2% (w/w), including as low as 1.6% (w/w) at 18-months room temperature (RT),
b. Impurity F was NMT 3% (w/w), including as low as 2.6% to 2.8% (w/w) at 18-months (RT),
c. Total Related Impurities (Excluding D-Epi) was NMT 4% (w/w), including as low as 3.2% to 3.4% (w/w) at 18-months (RT), and
d. API recovery was as high as 96.8%-97.0% at 18-months (RT).

Therefore, advantageously, Examples 1-3 demonstrate that even for junior epinephrine formulations with concentration levels of 0.1 mg/mL provided with no epinephrine overage, low total related impurities can be achieved using a relatively low concentration of antioxidant and a relatively low concentration of a metal-chelate agent compared to conventional commercial epinephrine formulations.

Examples 5-10: Effectiveness of Type and Amount of Antioxidant on Epinephrine Formulations The effectiveness of the type and amount of an antioxidant on reducing the impurities of epinephrine formulations was studied on Examples 5-10 as shown in Table 2 below. This study was conducted on each of Examples 5-10 with the following storage conditions: 3-months (40° Celsius), 6-months (RT), 12-months (RT), 18-months (RT), and 24-months (RT).

For Examples 5-10 in Table 2, each epinephrine formulation included L-Epinephrine as the API, sodium metabisulfite as the antioxidant, EDTA as the metal-chelate agent, sodium chloride as the tonicity agent, sodium citrate dihydrate and citric acid monohydrate as the buffer agents, and a pH of 3.8. Example 5 was prepared under an atmosphere of nitrogen to provide an aqueous solution of epinephrine (0.1 mg/ml), sodium chloride (6 mg/ml), sodium citrate dehydrate (0.395 mg/ml), citric acid monohydrate (1.613 mg/ml), EDTA (200 μg/ml), and sodium metabisulfite (0.075 mg/ml), and the pH of the aqueous solution was adjusted to pH 3.8 using HCl and NaOH. The solution was filtered through a 0.22 μm filter and the resultant solution was filled into a glass vial container having 13 mm rubber closure under nitrogen protection. Examples 6-8 were prepared in a manner similar to that described with respect to Example 5 except for using different concentrations of EDTA (100, 50, and 20 μg/ml, respectively).

Example 9 was prepared under an atmosphere of nitrogen to provide an aqueous solution of epinephrine (0.1 mg/ml), sodium chloride (6 mg/ml), sodium citrate dehydrate (0.395 mg/ml), citric acid monohydrate (1.613 mg/ml), EDTA (200 μg/ml), and sodium bisulfite (0.15 mg/ml), and the pH of the aqueous solution was adjusted to pH 3.8 using HCl and NaOH. The solution was filtered through a 0.22 μm filter and the resultant solution was filled into a glass vial container having a 13 mm rubber closure under nitrogen protection.

Example 10 was prepared under an atmosphere of nitrogen to provide an aqueous solution of epinephrine (0.1 mg/ml), sodium chloride (6 mg/ml), sodium citrate dehydrate (0.395 mg/ml), citric acid monohydrate (1.613 mg/ml), and sodium bisulfite (1 mg/ml), and the pH of the aqueous solution was adjusted to pH 3.0 using HCl and/or NaOH. The solution was filtered through a 0.22 μm filter and the resultant solution was filled into a glass vial container having a 13 mm rubber closure under nitrogen protection.

TABLE 2

Effectiveness of Type and Amount of Antioxidant on Epinephrine Formulations for Examples 5-10.

| | | | Example # | | | | | |
|---|---|---|---|---|---|---|---|---|
| | Ingredient | | Ex. 5 | Ex. 6 | Ex. 7 | Ex. 8 | Ex. 9 | Ex. 10 |
| 1 | API | L-Epinephrine, mg/mL | 0.1 | 0.1 | 0.1 | 0.1 | 0.1 | 0.1 |
| 2a | Antioxidant | Sodium metabisulfite, mg/mL | 0.075 | 0.075 | 0.075 | 0.075 | 0 | 0 |
| 2b | Antioxidant | Sodium bisulfite, mg/mL | 0 | 0 | 0 | 0 | 0.15 | 1 |
| 3 | Metal-chelator | Disodium Edetate (EDTA), μg/mL | 200 | 100 | 50 | 20 | 200 | 0 |
| 4 | Tonicity | Sodium Chloride, mg/mL | 6 | 6 | 6 | 6 | 6 | 6 |
| 5 | buffer agent | Sodium citrate dihydrate, mg/mL | 0.395 | 0.395 | 0.395 | 0.395 | 0.395 | 0.395 |
| 6 | buffer agent | Citric acid monohydrate, mg/mL | 1.613 | 1.613 | 1.613 | 1.613 | 1.613 | 1.613 |
| | pH | pH Unit | 3.8 | 3.8 | 3.8 | 3.8 | 3.8 | 3.0 |
| | Compounding Overage | | 0% | 0% | 0% | 0% | 0% | 0% |
| | API recovery, % (relative to API measured at 0 mo. at Room Temperature) | | | | | | | |
| | 40° C. 3 M | | 95.1% | 94.9% | 95.0% | 94.8% | 95.0% | 84.3% |
| | RT 6 M | | 98.6% | 98.6% | 98.5% | 98.4% | 95.9% | 91.7% |
| | RT 12 M | | 98.0% | 97.9% | 97.9% | 97.9% | 93.5% | 89.2% |

TABLE 2-continued

| Effectiveness of Type and Amount of Antioxidant on Epinephrine Formulations for Examples 5-10. | | | | | | |
|---|---|---|---|---|---|---|
| | Example # | | | | | |
| Ingredient | Ex. 5 | Ex. 6 | Ex. 7 | Ex. 8 | Ex. 9 | Ex. 10 |
| RT 18 M | 98.1% | 98.1% | 98.1% | 98.0% | 91.9% | 89.2% |
| RT 24 M | 96.4% | 96.3% | 96.3% | 96.3% | 88.4% | 85.7% |
| Enantiomeric Impurity: D-Epinephrine (D-Epi) | | | | | | |
| 40° C. 3 M | 2.5% | 2.5% | 2.5% | 2.7% | 2.5% | 5.5% |
| RT 6 M | 0.87% | 0.93% | 0.83% | 0.89% | 0.88% | 1.2% |
| RT 12 M | 1.4% | 1.4% | 1.4% | 1.4% | 1.3% | 2.2% |
| RT 18 M | 1.4% | 1.3% | 1.2% | 1.4% | 1.2% | 2.4% |
| RT 24 M | 1.8% | 1.8% | 1.8% | 1.8% | 1.7% | 3.5% |
| Epinephrine Sulfonic Acid (Impurity F) (w/w) | | | | | | |
| RT 6 M | 1.4% | 1.4% | 1.3% | 1.3% | 2.6% | 3.2% |
| RT 12 M | 2.1% | 2.1% | 2.2% | 2.2% | 2.3% | 6.1% |
| RT 18 M | 2.6% | 2.6% | 2.7% | 2.7% | 2.7% | 7.6% |
| RT 24 M | 3.5% | 3.6% | 3.6% | 3.7% | 2.7% | 9.9% |
| Total Related Impurities (Excluding D-Epi) (w/w) | | | | | | |
| RT 6 M | 1.6% | 1.5% | 1.5% | 1.5% | 3.1% | 5.8% |
| RT 12 M | 2.5% | 2.6% | 2.7% | 2.6% | 6.6% | 10.0% |
| RT 18 M | 3.5% | 3.5% | 3.8% | 3.4% | 8.1% | 11.3% |
| RT 24 M | 3.9% | 4.0% | 4.1% | 4.1% | 11.7% | 15.5% |

Advantageously, the impurity results of Examples 5-10 in Table 2 demonstrate that the type and amount of an antioxidant is effective in reducing the total related impurities of the presented epinephrine formulations.

First, as to the amount of an antioxidant, Examples 5-8 demonstrate that relatively low amounts of antioxidant, such as 0.075 mg/mL sodium metabisulfite, resulted in:

a. D-Epinephrine of NMT 2% (w/w) including as low as 1.8% (w/w) at 24-months (RT),
b. Impurity F was NMT 4% (w/w), including as low as 3.5%-3.7% (w/w) at 24-months (RT),
c. Total Related Impurities (Excluding D-Epi) was NMT 5% (w/w), including as low as 3.9%-4.1% (w/w) at 24-months (RT), and
d. API recovery as high as 96.4% (w/w) at 24-months (RT).

Advantageously, Examples 5-8 demonstrate that even for epinephrine formulations with low epinephrine concentration and no epinephrine overage, low total related impurities can be achieved with a low amount of antioxidant.

Second, as to the type of an antioxidant, Examples 9-10 had sodium bisulfite, at 0.15 mg/mL and 1 mg/mL, respectively, whereas Examples 5-8 had sodium metabisulfite as 0.075 mg/mL. As shown in the results in Table 2, sodium metabisulfite, even at lower amounts than sodium bisulfite in Examples 9-10, exhibited generally higher API recovery (%) and lower D-Epinephrine, Impurity F and Total Related Impurities (Excluding D-Epi). Thus, the type of antioxidant, specifically sodium metabisulfite, contributes to the reduction of impurities in epinephrine formulations having very low epinephrine concentrations.

Example 11-16: Epinephrine Formulations Also Works for a 10-ml Pre-Filled Syringe The effectiveness of the container and closure, specially a 10-mL prefilled syringe ("PFS") with rubber stopper, on reducing the impurities of epinephrine formulations was studied on Examples 11-16 as shown in Table 3 below. This study was conducted with the following storage conditions: 3-months (40° Celsius), 6-months (40° Celsius), 28-days (60° Celsius), 3-months (RT), 12-months (RT), 15-months (RT), 18-months (RT) and 24-months (RT). Note that results for 28-days (60° Celsius) was not available for Examples 14, 15 and 16, and 15 months (RT) and 18 months (RT) were not available for Example 16.

For Examples 11-16 in Table 3, each epinephrine formulation included L-Epinephrine as the API, sodium metabisulfite as the antioxidant, EDTA as the metal-chelate agent, sodium chloride as the tonicity agent, sodium citrate dihydrate and citric acid monohydrate as the buffer agents, and had a pH of 3.8.

Example 11 was prepared using bubble and blanket Water for Injection (WFI) with nitrogen gas. Citric acid monohydrate (6.0 mg/mL), sodium citrate dihydrate (6.0 mg/mL), sodium chloride (5.5 mg/mL), sodium metabisulfite (0.075 mg/mL), disodium edetate (2 μg/mL), and epinephrine (0.1 mg/mL) were added to and completely dissolved in water to provide an aqueous solution. The pH of the aqueous solution was adjusted to pH 3.8 using HCl and/or NaOH solutions. The resultant solution was filled into 10-mL PFS having a rubber stopper. Examples 12-13 were prepared in a manner similar to that described with respect to Example 11, except for different concentrations of EDTA (1 μg/mL, 5 μg/mL, respectively). Examples 14-15 were prepared in a manner similar to that described with respect to Example 11, except for different concentrations of sodium metabisulfite (0.05 mg/mL, 0.1 mg/mL, respectively). Example 16 was prepared in a manner similar to that described with respect to Example 11, except for different concentrations of sodium metabisulfite (0.05 mg/mL), sodium chloride (9 mg/mL), sodium citrate dihydrate (0.395 mg/mL), and citric acid monohydrate (1.613 mg/mL). Thus, Examples 11-16 were all contained in a 10-mL PFS with rubber stopper.

TABLE 3

| Effectiveness of Container and Closure on Epinephrine Formulations for Examples 11-16. | | | | | | | | |
|---|---|---|---|---|---|---|---|---|
| | | | Example # | | | | | |
| | Ingredient | | Ex. 11 | Ex. 12 | Ex. 13 | Ex. 14 | Ex. 15 | Ex. 16 |
| 1 | API | L-Epinephrine, mg/mL | 0.1 | 0.1 | 0.1 | 0.1 | 0.1 | 0.1 |
| 2 | Antioxidant | Sodium metabisulfite, mg/mL | 0.075 | 0.075 | 0.075 | 0.05 | 0.1 | 0.05 |
| 3 | Metal-chelator | Disodium Edetate (EDTA), μg/mL | 2 | 1 | 5 | 2 | 2 | 2 |
| 4 | Tonicity | Sodium Chloride, mg/mL | 5.5 | 5.5 | 5.5 | 5.5 | 5.5 | 9.0 |
| 5 | buffer agent | Sodium citrate dihydrate, mg/mL | 6.0 | 6.0 | 6.0 | 6.0 | 6.0 | 0.395 |
| 6 | buffer agent | Citric acid monohydrate, mg/mL | 6.0 | 6.0 | 6.0 | 6.0 | 6.0 | 1.613 |
| | pH | pH Unit | 3.8 | 3.8 | 3.8 | 3.8 | 3.8 | 3.8 |
| | Compounding Overage | | 0% | 0% | 0% | 0% | 0% | 0% |
| | API recovery, % (as label claim) | | | | | | | |
| | 40° C 3 M | | 98.3% | 98.8% | 98.3% | 99.7% | 100.9% | 101.1% |
| | 40° C 6 M | | 96.9% | 97.2% | 96.9% | 98.5% | 98.5% | 99.2% |
| | 60° C 28 Days | | 95.4% | 95.7% | 94.2% | N/A | N/A | N/A |
| | RT 3 M | | 100.3% | 100.6% | 100.4% | 101.6% | 103.3% | 102.5% |
| | RT 12 M | | 99.8% | 100.1% | 99.6% | 101.1% | 102.1% | 100.3% |
| | RT 15 M | | 99.3% | 99.7% | 99.5% | 100.7% | 101.8% | N/A |
| | RT 18 M | | 98.6% | 98.8% | 98.5% | 100.1% | 101.0% | N/A |
| | RT 24 M | | 97.9% | 98.0% | 98.0% | 99.3% | 100.3% | 99.7% |
| | Enantiomeric Impurity: D-Epinephrine (D-Epi) | | | | | | | |
| | 40° C. 3 M | | 3.6% | 3.3% | 2.9% | 3.0% | 3.3% | 4.2% |
| | 40° C. 6 M | | 7.3% | 7.1% | 6.7% | 7.2% | 7.0% | 7.2% |
| | RT 3 M | | 1.6% | 1.3% | 1.3% | 1.2% | 1.2% | 1.4% |
| | RT 12 M | | 1.9% | 1.9% | 1.8% | 1.9% | 1.9% | N/A |
| | RT 15 M | | 2.5% | 2.5% | 2.4% | 2.7% | 2.4% | N/A |
| | RT 18 M | | 2.8% | 2.7% | 2.5% | 2.8% | 2.7% | N/A |
| | RT 30 M | | 3.3% | 3.2% | N/A | 3.5% | 3.3% | N/A |
| | Epinephrine Sulfonic Acid (Impurity F) (w/w) | | | | | | | |
| | 40° C. 3 M | | 3.4% | 3.5% | 3.8% | 3.0% | 3.7% | 1.8% |
| | 40° C. 6 M | | 4.8% | 5.0% | 5.5% | 4.5% | 6.3% | 2.7% |
| | RT 3 M | | 0.65% | 0.69% | 0.72% | 0.60% | 0.71% | 0.31% |
| | RT 12 M | | 1.8% | 1.9% | 2.0% | 1.7% | 2.0% | 1.2% |
| | RT 15 M | | 2.8% | 2.8% | 3.0% | 2.4% | 3.0% | N/A |
| | RT 18 M | | 3.4% | 3.4% | 3.7% | 2.9% | 3.6% | N/A |
| | RT 24 M | | 4.4% | 4.5% | 4.6% | 3.7% | 4.6% | N/A |
| | Total Related Impurities (Excluding D-Epi) (w/w) | | | | | | | |
| | 40° C. 3 M | | 4.2% | 4.3% | 4.6% | 3.7% | 4.6% | 2.0% |
| | 40° C. 6 M | | 6.2% | 6.5% | 7.1% | 5.8% | 8.1% | 3.3% |
| | RT 3 M | | 0.80% | 0.91% | 0.98% | 0.81% | 1.0% | 0.31% |
| | RT 12 M | | 2.2% | 2.3% | 2.5% | 2.0% | 2.5% | 1.3% |
| | RT 15 M | | 3.4% | 3.4% | 3.5% | 2.8% | 3.5% | N/A |
| | RT 18 M | | 3.9% | 3.9% | 4.3% | 3.3% | 4.3% | N/A |
| | RT 24 M | | 5.4% | 5.5% | 5.5% | 4.3% | 5.7% | N/A |

Surprisingly and advantageously, the impurity results in Table 3 demonstrate that low amounts of antioxidant, such as 0.05-0.075 mg/mL sodium metabisulfite and low amounts of metal-chelate agent, such as 1-5 μg/ml EDTA, are effective in reducing impurities for Examples 11-15. In particular, as demonstrated in Table 3, Examples 11-15 exhibited:

a. Enantiomeric Impurity, D-Epinephrine (D-Epi) of NMT 4% (w/w), including as low as 3.2%-3.5% (w/w) at 30-months (RT), b. Impurity F was NMT 5% (w/w), including as low as 3.7%-4.6% (w/w) at 24-months (RT), c. Total Related Impurities (Excluding D-Epi) was NMT 6% (w/w), including as low as 4.3%-5.7% (w/w) at 24-months (RT), and d. API recovery was as high as 97.9% or greater at 24-months (RT).

Therefore, advantageously, Examples 11-15 demonstrate that even for epinephrine formulations with very low epinephrine concentration and no epinephrine overage, low total related impurities can be achieved using a very low concentration of antioxidant and a low concentration of a metal-chelate agent.

Example 17-19: Comparative Examples with Epinephrine Formulation Having 14% Overage, Very High Levels of Impurity F and Total Related Impurities Examples 17-19 are comparative examples and specifically, epinephrine formulations having 14% overage. This study was conducted with the following storage conditions: 3-months (40° C.), 0-month (RT), 6-months (RT), 12-months (RT), and 18-months (RT).

As shown in Table 4, Examples 17-19 all had the same epinephrine formulation in an effort to conduct repeat studies. Notably, Examples 17-19 had an epinephrine overage of 14%, which means the API, L-Epinephrine, had an initial concentration of 0.114 mg/mL.

Examples 17-19 were prepared using bubble and blanket Water for Injection (WFI) with nitrogen gas. Citric acid monohydrate (1.613 mg/mL), sodium citrate dihydrate (0.395 mg/mL), sodium chloride (6 mg/mL), sodium bisulfite (1 mg/mL), and epinephrine (0.114 mg/mL) were added to and completely dissolved in water to provide an aqueous solution. The pH of the aqueous solution was adjusted to pH 2.75 using an HCl solution. The solution was filtered through a 0.2 μm filter and filled into 10-mL prefilled syringe (PFS) having a rubber stopper. Examples 17-19 were at scale-up lots.

TABLE 4

| Epinephrine Formulations with API Overage | | | | | |
|---|---|---|---|---|---|
| Ingredient (mg/mL, or specified) | | | Ex. 17 | Ex. 18 | Ex. 19 |
| 1 | API | L-Epinephrine, mg/mL | 0.1 | 0.1 | 0.1 |
| 2a | Antioxidant | Sodium metabisulfite, mg/mL | — | — | — |
| 2b | | Sodium bisulfite | 1 | 1 | 1 |
| 3 | Metal-chelator | Di sodium Edetate (EDTA), μg/mL | — | — | — |
| 4 | Tonicity | Sodium Chloride, mg/mL | 6 | 6 | 6 |
| 5 | buffer agent | Sodium citrate dihydrate, mg/mL | 0.395 | 0.395 | 0.395 |
| 6 | buffer agent | Citric acid monohydrate, mg/mL | 1.613 | 1.613 | 1.613 |
| | pH | pH Unit | 2.75 | 2.75 | 2.75 |
| Compounding Overage | | | 14% | 14% | 14% |
| API recovery, % (as label claim) | | | | | |
| | 40° C. 3 M | | 102.6% | 103.0% | 101.1% |
| | RT 0 | | 113.9% | 113.8% | 114.0% |
| | RT 6 M | | 108.1% | 108.3% | 108.2% |
| | RT 12 M | | 103.2% | 102.2% | 103.1% |
| | RT 18 M | | 98.7% | 99.1% | 99.9% |
| Enantiomeric Impurity: D-Epinephrine (D-Epi) | | | | | |
| | 40° C. 3 M | | 2.8% | 3.1% | 3.6% |
| | RT 0 | | 0.90% | 0.96% | 1.20% |
| | RT 6 M | | 1.5% | 1.7% | 1.9% |
| | RT 12 M | | 1.9% | 2.0% | 2.6% |
| | RT 18 M | | 2.2% | 2.4% | 2.6% |
| Epinephrine Sulfonic Acid (Impurity F) (w/w) | | | | | |
| | 40° C. 3 M | | 13.8% | 14.5% | 16.2% |
| | RT 0 | | 0.34% | 0.36% | 0.33% |
| | RT 6 M | | 5.8% | 5.8% | 6.0% |
| | RT 12 M | | 12.0% | 10.5% | 11.8% |
| | RT 18 M | | 16.3% | 15.4% | 15.9% |
| Total Related Impurities (Excluding D-Epi) (w/w) | | | | | |
| | 40° C. 3 M | | 16.0% | 16.6% | 18.6% |
| | RT 0 | | 0.75% | 0.76% | 0.77% |
| | RT 6 M | | 7.5% | 7.4% | 7.6% |
| | RT 12 M | | 15.3% | 13.1% | 14.5% |
| | RT 18 M | | 20.9% | 19.2% | 19.2% |

Thus, disadvantageously, the impurity results in Table 4 demonstrate that Examples 17-19 could not produce impurities as low as the aforementioned Examples 1-3, 5-8, 11-15. In particular, for Examples 17-19, Impurity F was generally higher than 10% (w/w) and as high as 16.3% at 18-months (RT). Similarly, Total Related Impurities (Excluding D-Epi) was generally higher than 15.0% (w/w) and as high as 20.9% at 18-months (RT). Therefore, Examples 1-3, 5-8, 11-15 advantageously provided significantly lower impurities as compared to Examples 17-19.

FIG. 1 depicts a chart showing the percentage of Impurity F for Examples 17-19. To generate extrapolated data points after a duration of 18 months, the available stability data (e.g., at define duration intervals of 0 mo., 6 mo., 12 mo., and up to 18 mo., all at RT) were plotted and forecasted to generate the 30 mo. stability test results with a 95% confidence interval using Predicator™ software. As shown, the data provided in the charts up to 18-months at RT has been extrapolated as discussed for a duration of 30 months at RT. As shown, it is estimated that at 30 months storage at RT, each of Examples 17-19 would contain over 25% w/w of Impurity F.

Figure 2:
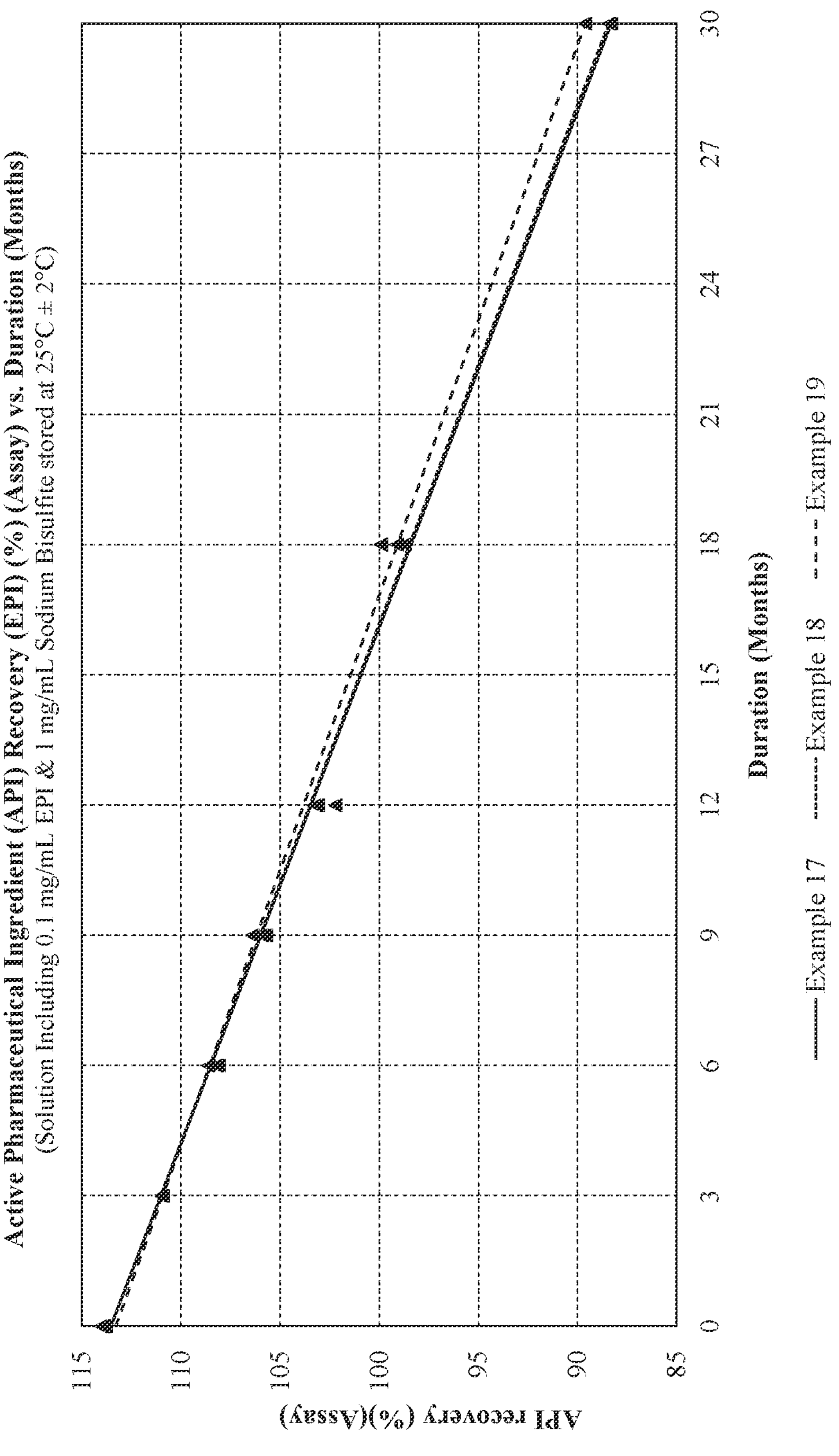
FIG. 2 depicts a graph showing API recovery (%) (assay) over time at a storage temperature of 25° C.±2° C. for Examples 17-19 as disclosed herein.

FIG. 2 depicts a chart showing the API recovery percentage for Examples 17-19. As shown, the data provided in Table 4 up to 18-months at RT has been extrapolated as discussed for a duration of up to 30 months RT. As shown, it is estimated that at 30 months storage at RT, each of Examples 17-19 would have API recoveries under 90%.

Examples 20-22: Stability of Epinephrine Formulations

Stability fill lots shown as Examples 20, 21, and 22 were prepared in a manner similar to that described with respect to Example 1 except for using 0.075 mg/mL antioxidant, such as sodium metabisulfite, and 4 μg/mL metal-chelate agent, such as EDTA. The details of Examples 20-22 are shown in Table 5. The effectiveness of the container and closure, specially a 10-mL prefilled syringe ("PFS") with rubber stopper, on reducing the impurities of epinephrine formulations was studied (as provided in Example 11-16). The PFSs were stored inverted (In) or upright (Up).

TABLE 5

| Epinephrine Formulations with for stability fill lots | | | | | | | |
|---|---|---|---|---|---|---|---|
| | | Example# | | | | | |
| Ingredient | | 20 | | 21 | | 22 | |
| API | L-Epinephrine, mg/mL | 0.1 | | 0.1 | | 0.1 | |
| Antioxidant | Sodium metabisulfite, mg/mL | 0.075 | | 0.075 | | 0.075 | |
| Metal-chelator | Disodium Edetate (EDTA), µg/mL | 4 | | 4 | | 4 | |
| Tonicity | Sodium Chloride, mg/mL | 8.2 | | 8.2 | | 8.2 | |
| buffer agent | Sodium citrate dihydrate, mg/mL | 1.5 | | 1.5 | | 1.5 | |
| buffer agent | Citric acid monohydrate, mg/mL | 3.3 | | 3.3 | | 3.3 | |
| pH | pH Unit | 3.8 | | 3.8 | | 3.8 | |
| Compounding Overage | | 0% | | 0% | | 0% | |
| API recovery, % (as label claim) | | | | | | | |
| | | In. | Up. | In. | Up. | In. | Up. |
| RT 0 M | | 100.4% | | 100.3% | | 100.5% | |
| RT 3 M | | 99.0% | 99.3% | 99.2% | 99.2% | 99.3% | 99.3% |
| RT 6 M | | 98.9% | 98.7% | 98.7% | 98.7% | 99.0% | 99.2% |
| RT 9 M | | 98.3% | 98.4% | 98.6% | 99.1% | 99.0% | 99.0% |
| RT 12 M | | 97.7% | 97.9% | 97.3% | 97.5% | 98.0% | 97.8% |
| RT 18 M | | 96.9% | 97.0% | 97.0% | 97.0% | 97.4% | 97.5% |
| 30° C 3 M | | 99.1% | 98.5% | 98.7% | 98.4% | 99.1% | 99.0% |
| 30° C 6 M | | 98.0% | 98.0% | 97.9% | 97.9% | 98.2% | 98.3% |
| 30° C 9 M | | 97.1% | 97.4% | 97.2% | 97.3% | 97.4% | 97.7% |
| 30° C 12 M | | 96.0% | 96.5% | 95.7% | 95.8% | 96.0% | 96.7% |
| 40° C 1 M | | 100.0% | 100.2% | 99.6% | 99.7% | 99.8% | 99.8% |
| 40° C 2 M | | 97.8% | 97.9% | 97.7% | 98.2% | 98.3% | 98.0% |
| 40° C 3 M | | 96.8% | 96.6% | 97.2% | 96.8% | 97.4% | 97.1% |
| 40° C 6 M | | 93.9% | 94.6% | 94.5% | 95.3% | 94.5% | 95.7% |
| Enantiomeric Impurity: D-Epinephrine (D-Epi) | | | | | | | |
| | | In. | Up. | In. | Up. | In. | Up. |
| RT 0 | | 1.2% | | 1.1% | | 1.1% | |
| RT 6 M | | 1.9% | 1.9% | 1.8% | 1.8% | 1.7% | 1.8% |
| RT 12 M | | 2.4% | 2.3% | 2.4% | 2.4% | 2.3% | 2.3% |
| RT 18 M | | 2.2% | 2.2% | 2.1% | 2.2% | 2.1% | 2.1% |
| 30° C 6 M | | 2.3% | 2.3% | 2.2% | 2.2% | 2.2% | 2.2% |
| 30° C 12 M | | 3.3% | 3.3% | 3.2% | 3.2% | 3.3% | 3.1% |
| 40° C 1 M | | 1.5% | 1.5% | 1.4% | 1.5% | 1.4% | 1.4% |
| 40° C 2 M | | 2.5% | 2.5% | 2.4% | 2.6% | 2.4% | 2.4% |
| 40° C 3 M | | 3.1% | 3.2% | 3.0% | 3.2% | 2.9% | 3.0% |
| 40° C 6 M | | 5.2% | 5.2% | 4.7% | 5.3% | 5.0% | 5.6% |
| Epinephrine Sulfonic Acid (Impurity F) (w/w) | | | | | | | |
| | | In. | Up. | In. | Up. | In. | Up. |
| RT 0 M | | 0.36% | | 0.34% | | 0.30% | |
| RT 12 M | | 3.1% | 3.0% | 3.1% | 3.0% | 3.0% | 3.0% |
| RT 18 M | | 4.6% | 4.5% | 4.6% | 4.5% | 4.4% | 4.4% |
| 30° C 12 M | | 5.4% | 5.0% | 5.3% | 5.3% | 5.1% | 4.9% |
| 40° C 3 M | | 4.8% | 4.9% | 4.7% | 4.9% | 4.5% | 4.6% |
| 40° C 6 M | | 8.6% | 8.1% | 8.0% | 7.7% | 7.8% | 6.8% |

TABLE 5-continued

| Epinephrine Formulations with for stability fill lots | | | | | | |
|---|---|---|---|---|---|---|
| Total Related Impurities (Excluding D-Epi) (w/w) | | | | | | |
| | In. | Up. | In. | Up. | In. | Up. |
| RT 0 M | 0.51% | | 0.44% | | 0.40% | |
| RT 12 M | 3.6% | 3.4% | 3.6% | 3.4% | 3.6% | 3.4% |
| RT 18 M | 5.4% | 5.0% | 5.4% | 5.1% | 5.2% | 5.0% |
| 30° C 12 M | 6.4% | 5.6% | 6.4% | 6.1% | 6.1% | 5.7% |
| 40° C 3 M | 5.7% | 5.7% | 5.6% | 5.7% | 5.4% | 5.4% |
| 40° C 6 M | 10.4% | 9.7% | 9.8% | 9.3% | 9.7% | 8.3% |

Surprisingly and advantageously, the impurity results in Table 5 demonstrate that low amounts of antioxidant, such as 0.075 mg/mL sodium metabisulfite and low amounts of metal-chelate agent, such as 4 μg/ml EDTA, are effective in reducing impurities for Examples 20-22.

In particular, as demonstrated in Table 5, the samples for Examples 20-22 exhibited:

a. Enantiomeric Impurity, D-Epinephrine (D-Epi) of NMT 3%, including as low as 2.1% to 2.2% (w/w) at 18-months (RT),
b. Impurity F of NMT 5% (w/w), including as low as 4.4%-4.6% (w/w) at 18-months (RT),
c. Total related impurities (excluding D-Epi) of NMT 6% (w/w), including as low as 5.0%-5.4% (w/w) at 18-months (RT), and
d. API recovery was as high as 96.9% to 97.5% (w/w) at 18-months (RT). Potential variance between detection of total related impurities and API recovery are discussed in at least Para. [0092]-[0095] above. The discussed methods are used to test API recovery, D-Epinephrine, and total related impurities. Each of the included ingredients in the presently disclosed formulations may have different and/or distinct responses and/or absorbance spectra behavior depending on the corresponding detection methods ultraviolet (UV) wavelength used. Note: the discussed test methods have been validated and referenced relative to USP and EP. In this way, the wavelengths have been established as suitable for their specific corresponding tests. As a result, different test wavelengths are expected to produce difference sensitivity for each tested-for compound, which (in some instances) may result in potential variances leading to a sum of total related impurities added to API recovery not equaling 100% (e.g., exceeding 100%). Instances of recovery exceeding 100% typically are considered to be negligible in chromatography-based experimentation.

Figure 3:
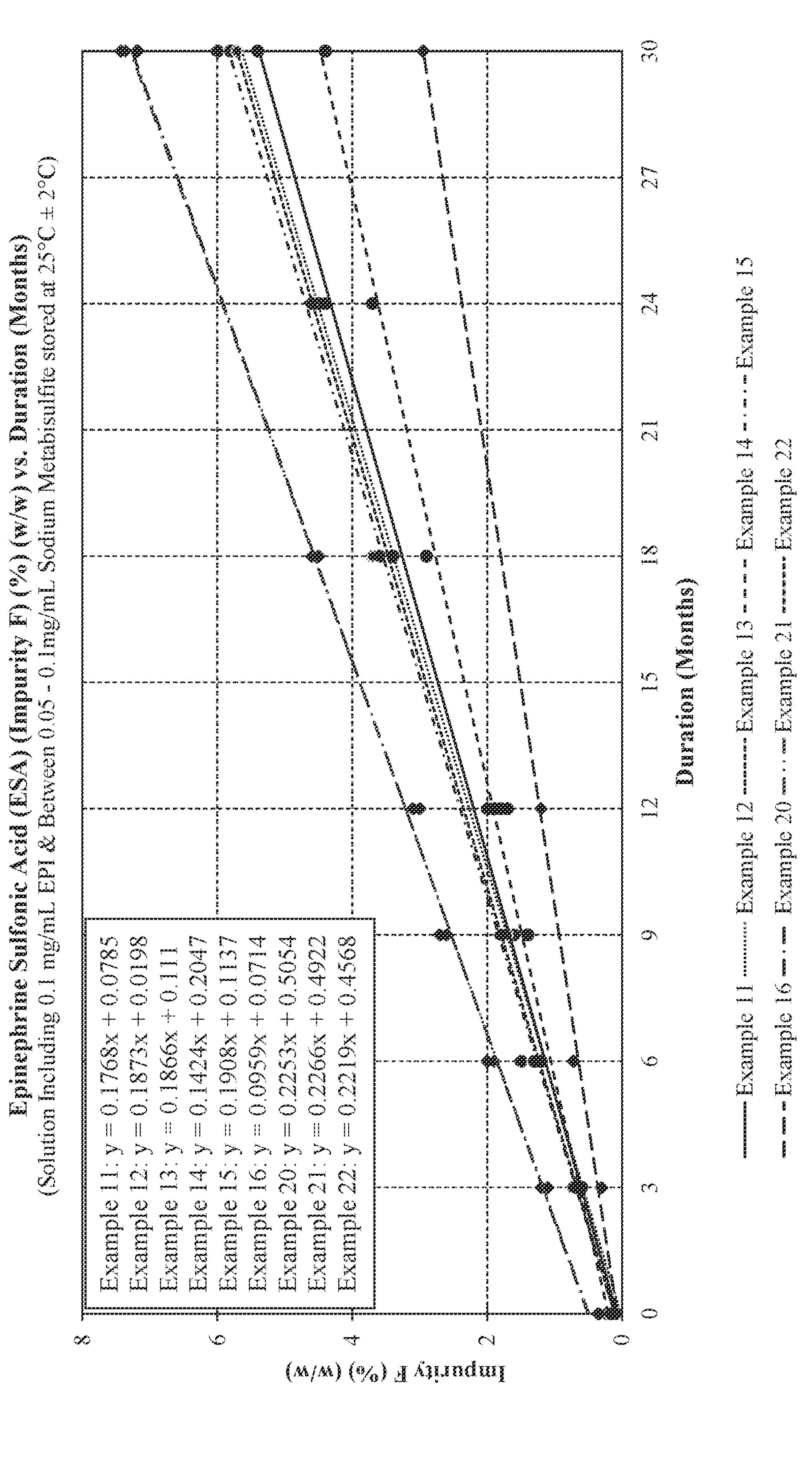
FIG. 3 depicts a graph showing the amount of Impurity F (%) over time at a storage temperature of 25° C.±2° C. for Examples 11-16 and Examples 20-22 as disclosed herein.

FIG. 3 depicts a graph showing the percentage of Impurity F for Examples 11-16 and 20-22. As shown, the data provided in Table 3 up to 24 months RT and Table 5 up to 18 months RT has been extrapolate for a duration of 30 months RT. As shown, it is estimated that Impurity F for these Examples remains well below 8% w/w even at time periods of 24-30 months at RT.

Figure 4:
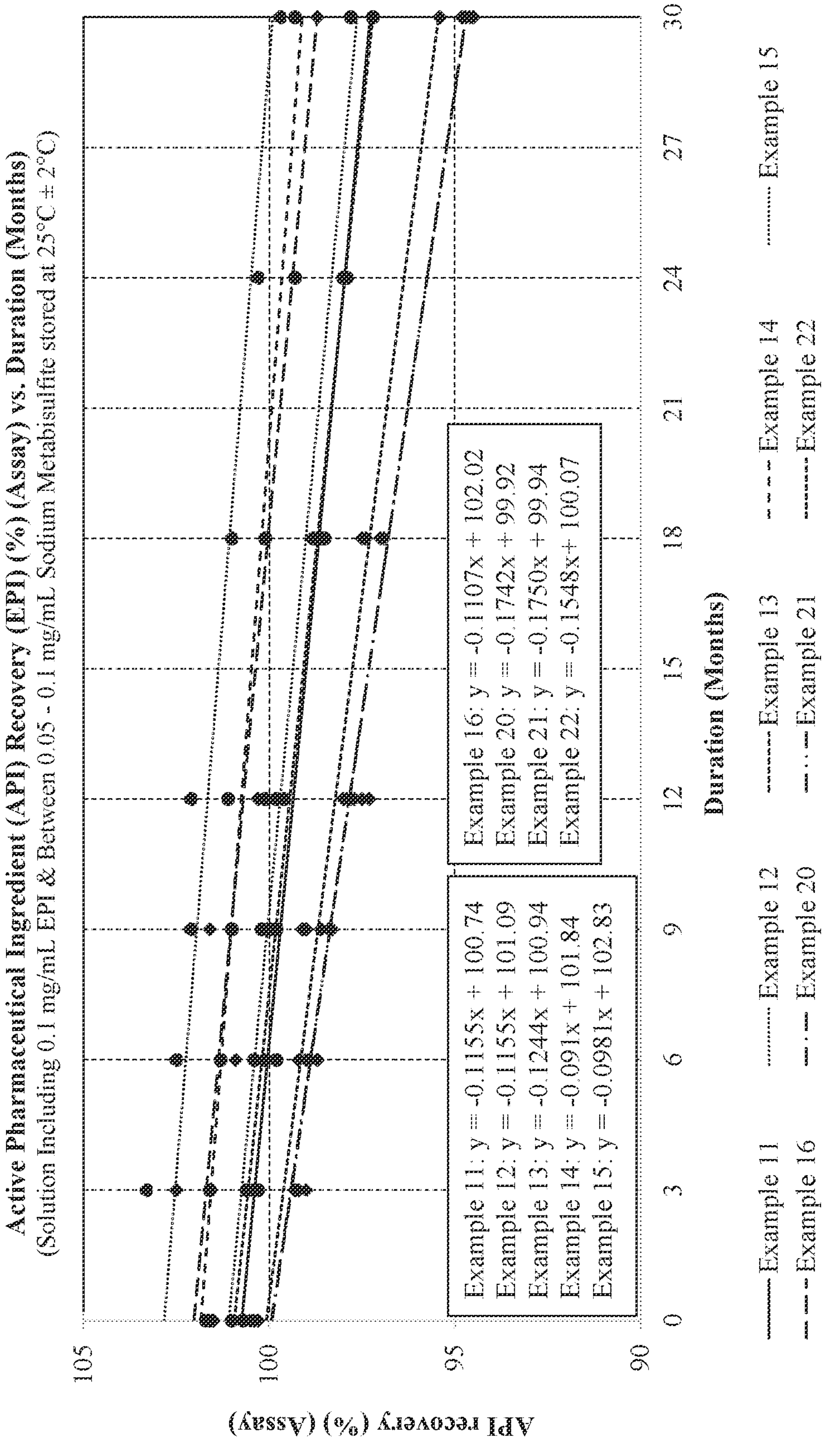
FIG. 4 depicts a graph showing API recovery (%) over time at a storage temperature of 25° C.±2° C. for Examples 11-16 and Examples 20-22 as disclosed herein.

FIG. 4 depicts a chart showing the API recovery percentage for Examples 11-16 and 20-22. As shown, the data provided in Table 3 up to 24-months at RT and Table 5 up to 18-months at RT has been extrapolated for a duration of up to 30 months RT. As shown, it is estimated that at 30 months storage at RT, each of Examples 11-16 and 20-22 have API recoveries well over 90%, such as about 95% or greater. Specifically, in embodiments the formulations have an API recovery of at least about 95%, such as at least about 96%, such as at least about 97%, such as at least about 98% for a time period of about 30-months RT.

Figure 5:
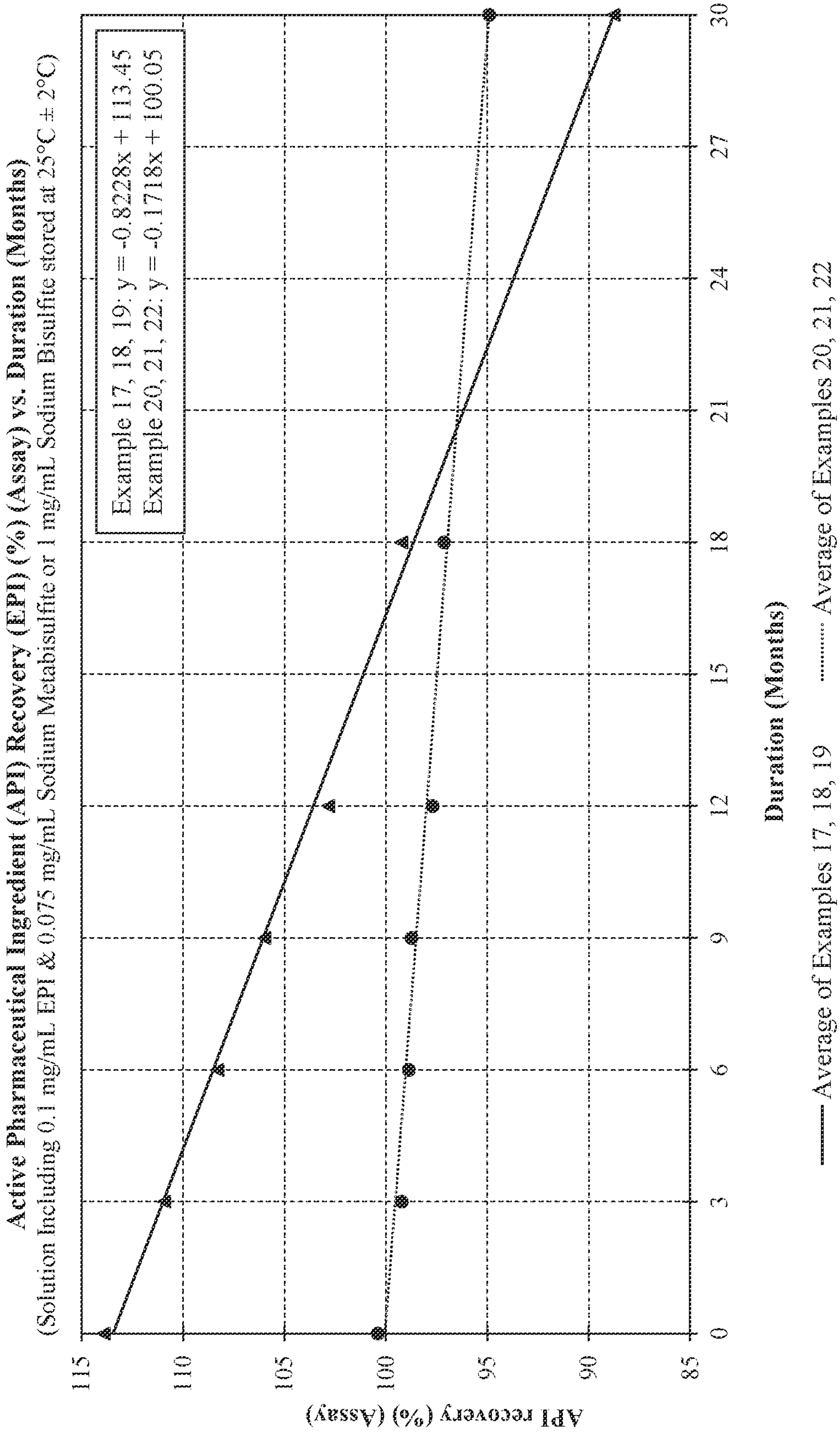
FIG. 5 depicts a graph showing API recovery (%) over time at a storage temperature of 25° C.±2° C. for Examples 17-19 and Examples 20-22.

FIG. 5 depict the percentage of API recovery over time for Examples 17-19 in comparison to Examples 20-22. As shown, Examples 17-19 have much lower API recoveries at 21-30 months, despite being formulated with an overage. Examples 20-22, which do not have any epinephrine overage, have API recoveries of at least about 95% at a storage period of 30-months RT.

Figure 6:
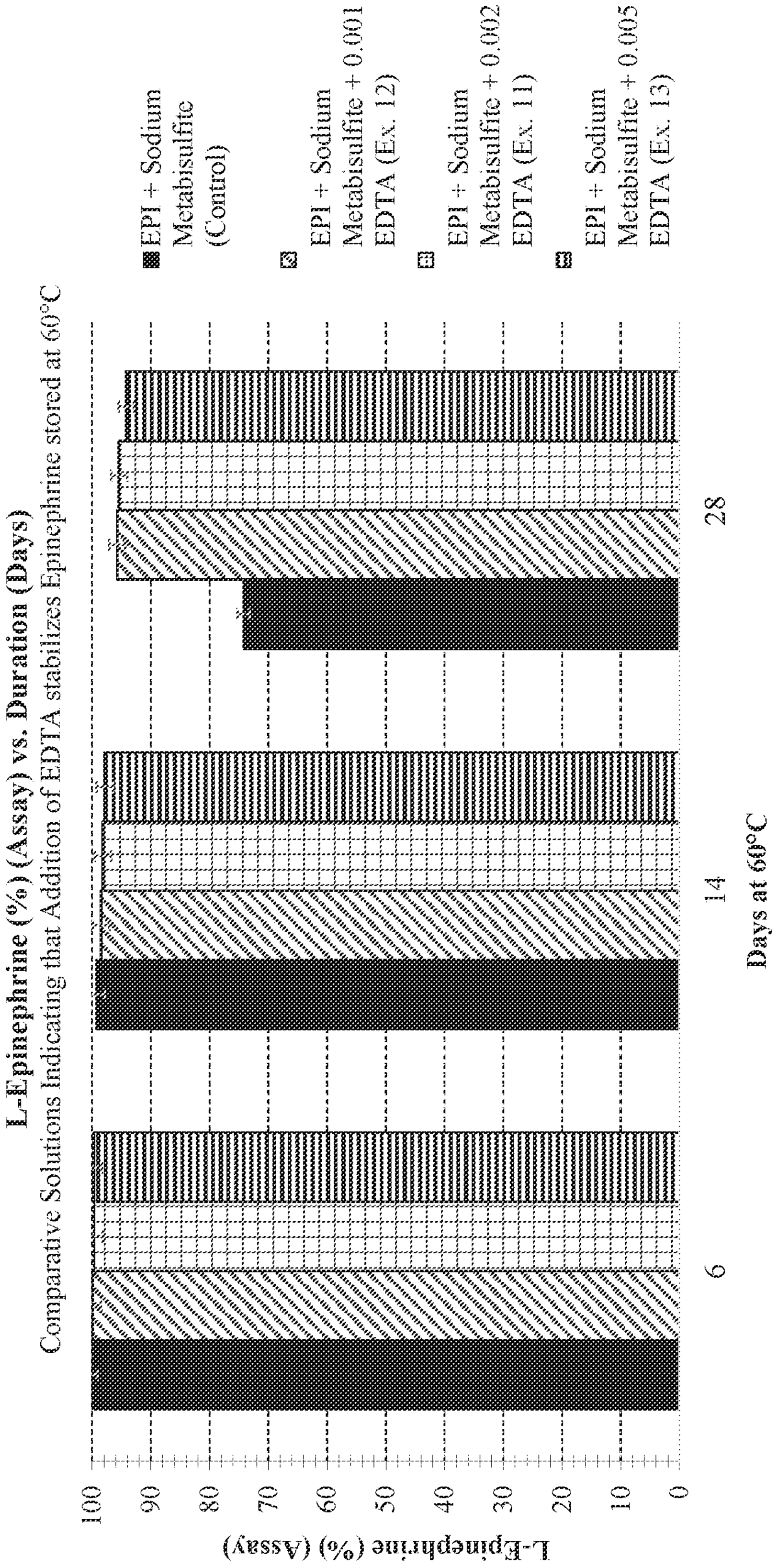
FIG. 6 depicts a graph showing L-epinephrine (%) recovery for a control epinephrine formulation and Examples 11-13 at different storage days at a storage temperature of 60° C.

FIG. 6 depicts L-epinephrine recovery for Examples 11-13 as compared to a control epinephrine formulation. The control epinephrine formulation denoted "EPI+Sodium metabisulfite" contains 0.1 mg/mL epinephrine, 0.395 mg/mL sodium citrate dihydrate, 1.613 mg/mL citric acid monohydrate, 9.0 mg/mL sodium chloride, 0.05 mg/mL sodium metabisulfite, and no (0 mg/mL) EDTA. As shown, at 28-days storage at 60° C., Examples 11-13 continue to have L-epinephrine recovery rates well above 90%, whereas the epinephrine formulation without EDTA has an L-epinephrine recovery of under 80%, such as at or under 75%. Notably, the 6-day data for the control formulation is extrapolated from actual 14-day and 28-day data. For Examples 11-13, the 6-day and 14-day data is extrapolated from the actual 28-day data.

Examples 23-29: Stability of Epinephrine Formulations with Varying Amounts of Antioxidant Example 23 was prepared under an atmosphere of nitrogen to provide an aqueous solution of L-Epinephrine (0.1 mg/mL), sodium chloride (6 mg/mL), sodium citrate dihydrate (0.6 mg/mL), citric acid monohydrate (2 mg/mL), EDTA (4 μg/mL), and sodium metabisulfite (0.04 mg/mL), and the pH of the aqueous solution was adjusted to pH 3.8 using HCl and NaOH. The aqueous solution was filtered through a 0.22 μm filter and the resultant solution was filled into a glass vial container having a 13 mm rubber closure under nitrogen protection. Examples 24-25 were prepared in a manner similar to that described with respect to Example 23 except for using different concentrations of sodium metabisulfite (0.08 mg/mL and 0.46 mg/mL, respectively). Example 26 was prepared in a manner similar to that described with respect to Example 24 except for using different pH=3.3. Example 27 was prepared in a manner similar to that described with respect to Example 23 except for using zero amount of EDTA (0 μg/mL). Example 29 was prepared in a manner same to that described with respect to Example 10.

Example 28 was prepared under an atmosphere of nitrogen to provide an aqueous solution of L-Epinephrine (0.1 mg/mL), sodium chloride (8.16 mg/mL), sodium citrate dihydrate (0.6 mg/mL), citric acid monohydrate (2.19 mg/ml) and sodium metabisulfite (0.46 mg/mL), and the pH of the aqueous solution was adjusted to pH 3.3 using HCl and NaOH. The aqueous solution was filtered through a 0.22 µm filter and the resultant solution was filled into a glass vial container having a 13 mm rubber closure under nitrogen protection. In some embodiments, Example 28 may be prepared to have identical or substantially similar excipients as one or more products marketed by Hospira, a former pharmaceutical and medical device company now wholly-owned by Pfizer Hospital US of Lake Forest, IL.

TABLE 6

Epinephrine Formulations with varying amounts of antioxidant

| Ingredient (mg/mL, or specified) | | | Example # 23 | 24 | 25 | 26 | 27 | 28 | 29 |
|---|---|---|---|---|---|---|---|---|---|
| 1 | API | L-Epinephrine, mg/mL | 0.1 | 0.1 | 0.1 | 0.1 | 0.1 | 0.1 | 0.1 |
| 2 | Antioxidant | Sodium metabisulfite, mg/mL | 0.04 | 0.08 | 0.46 | 0.08 | 0.08 | 0.46 | 0 |
| 3 | Antioxidant | Sodium bisulfite mg/mL | 0 | 0 | 0 | 0 | 0 | 0 | 1 |
| 3 | Metal-chelator | Disodium Edetate (EDTA), µg/mL | 4 | 4 | 4 | 4 | 0 | 0 | 0 |
| 4 | Tonicity | Sodium Chloride, mg/mL | 6 | 6 | 6 | 6 | 6 | 8.16 | 6 |
| 5 | buffer agent | Sodium citrate dihydrate, mg/mL | 0.6 | 0.6 | 0.6 | 0.6 | 0.6 | 0.6 | 0.395 |
| 6 | buffer agent | Citric acid monohydrate, mg/mL | 2 | 2 | 2 | 2 | 2 | 2.19 | 1.613 |
| | pH | pH Unit | 3.8 | 3.8 | 3.8 | 3.3 | 3.8 | 3.3 | 3 |
| | Compounding Overage | | 0% | 0% | 0% | 0% | 0% | 0% | 0% |
| API recovery, % (relative to API measured at 0 months at Room Temperature) | | | | | | | | | |
| | 60° C. at 1 week | | 96.08 | 95.33 | 93.14 | 94.43 | 94.04 | 92.37 | 91.03 |
| | 60° C. at 2 weeks | | 93.38 | 92.31 | 89.42 | 91.22 | 91.60 | 88.14 | 85.39 |
| | 60° C. at 3 weeks | | 90.30 | 88.55 | 84.08 | 87.40 | 86.07 | 81.83 | 77.75 |
| | 60° C. at 4 weeks | | 87.62 | 86.32 | 79.56 | 84.24 | 81.03 | 77.12 | 72.23 |
| | 40° C. 1 M | | 98.72 | 98.51 | 97.27 | 97.98 | 97.32 | 96.75 | 96.28 |
| | 40° C. 2 M | | 97.00 | 96.40 | 94.87 | 96.21 | 93.89 | 93.81 | 92.84 |
| | 40° C. 3 M | | 95.34 | 94.42 | 92.56 | 93.86 | 92.19 | 90.74 | 88.37 |
| | 40° C. 4 M | | 94.70 | 93.38 | 91.26 | 92.86 | 91.17 | 88.81 | 86.35 |
| | 40° C. 5 M | | 94.01 | 93.24 | 89.57 | 91.63 | 88.73 | 86.30 | 84.41 |
| | 40° C. 6 M | | 92.66 | 90.39 | 87.13 | 89.85 | 86.80 | 84.26 | 81.05 |
| | RT 3 M | | 99.21 | 99.09 | 98.57 | 99.00 | 98.76 | 98.16 | 97.99 |
| | RT 6 M | | 98.89 | 98.73 | 97.86 | 98.45 | 98.00 | 96.90 | 97.01 |
| | RT 24 M | | 97.15 | 96.32 | 93.97 | 96.72 | 93.90 | 92.73 | 90.71 |

Surprisingly and advantageously, the API recovery rates in Table 6 demonstrate that low amounts of antioxidant, such as 0.04 mg/mL-0.08 mg/mL of sodium metabisulfite are effective in reducing impurities for Examples 23-24.

In particular, as demonstrated in Table 6, Examples 23-24 exhibited API recoveries was as high as 96.32%-97.15% (w/w) at 24-months (RT).

Figure 7:
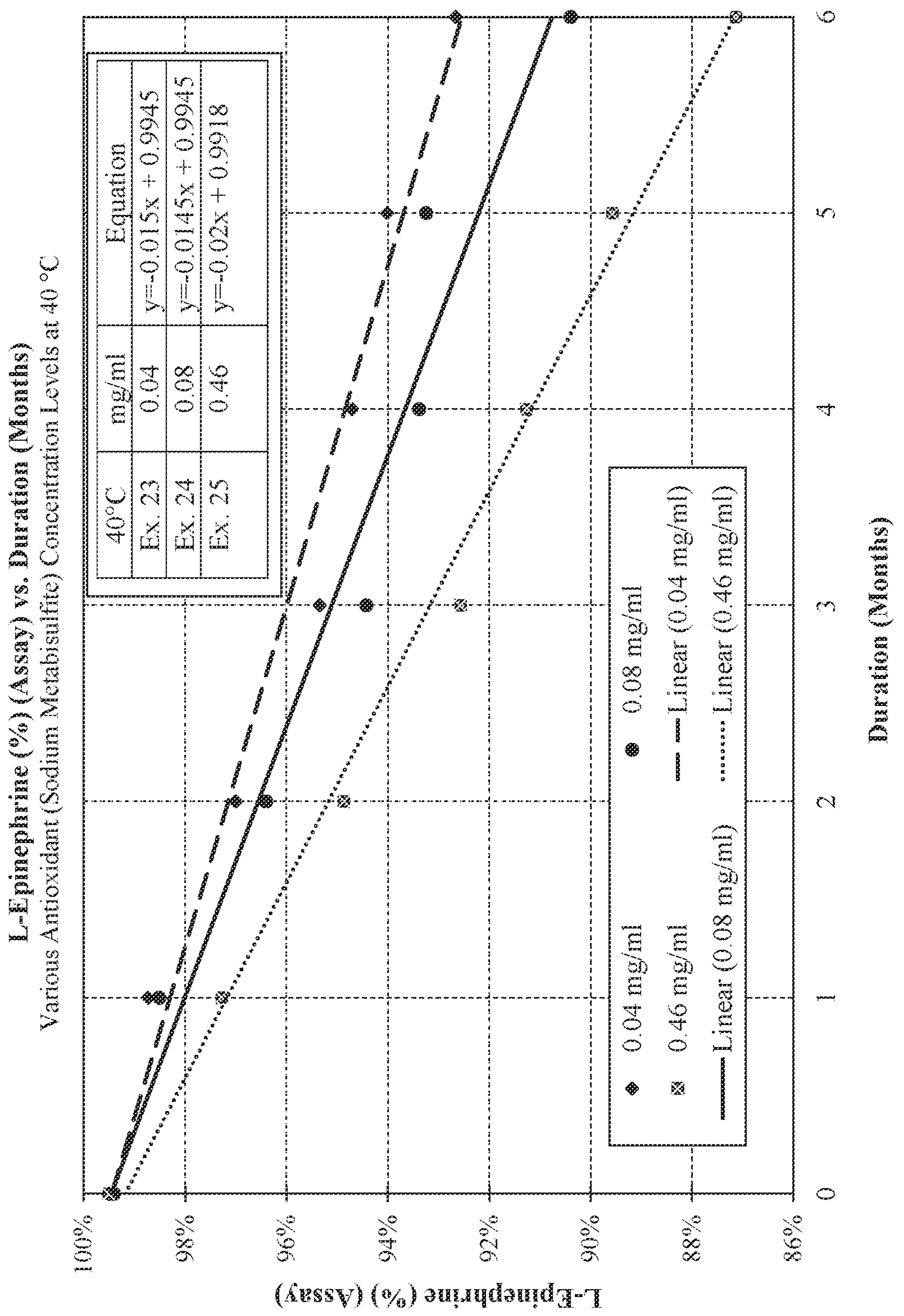
FIG. 7 depicts a graph showing L-epinephrine (%) recovery over time for Examples 23-25 at a storage temperature of 40° C.

FIG. 7 depicts a graph showing the L-epinephrine (%) w/w recovery for Examples 23-25 up to 6 months at 40° C. As shown, L-epinephrine (%) recovery is much higher for Examples 23-24, each having 0.04 mg/mL and 0.08 mg/ml, respectively of sodium metabisulfite. For example, both Examples 23 and 24 have L-epinephrine recovery percentages greater than 90% at 6 months storage at 40° C. Example 25 having 0.46 mg/mL of sodium metabisulfite has an L-epinephrine % recovery of less than 88% at 6 months storage at 40° C.

Figure 8:
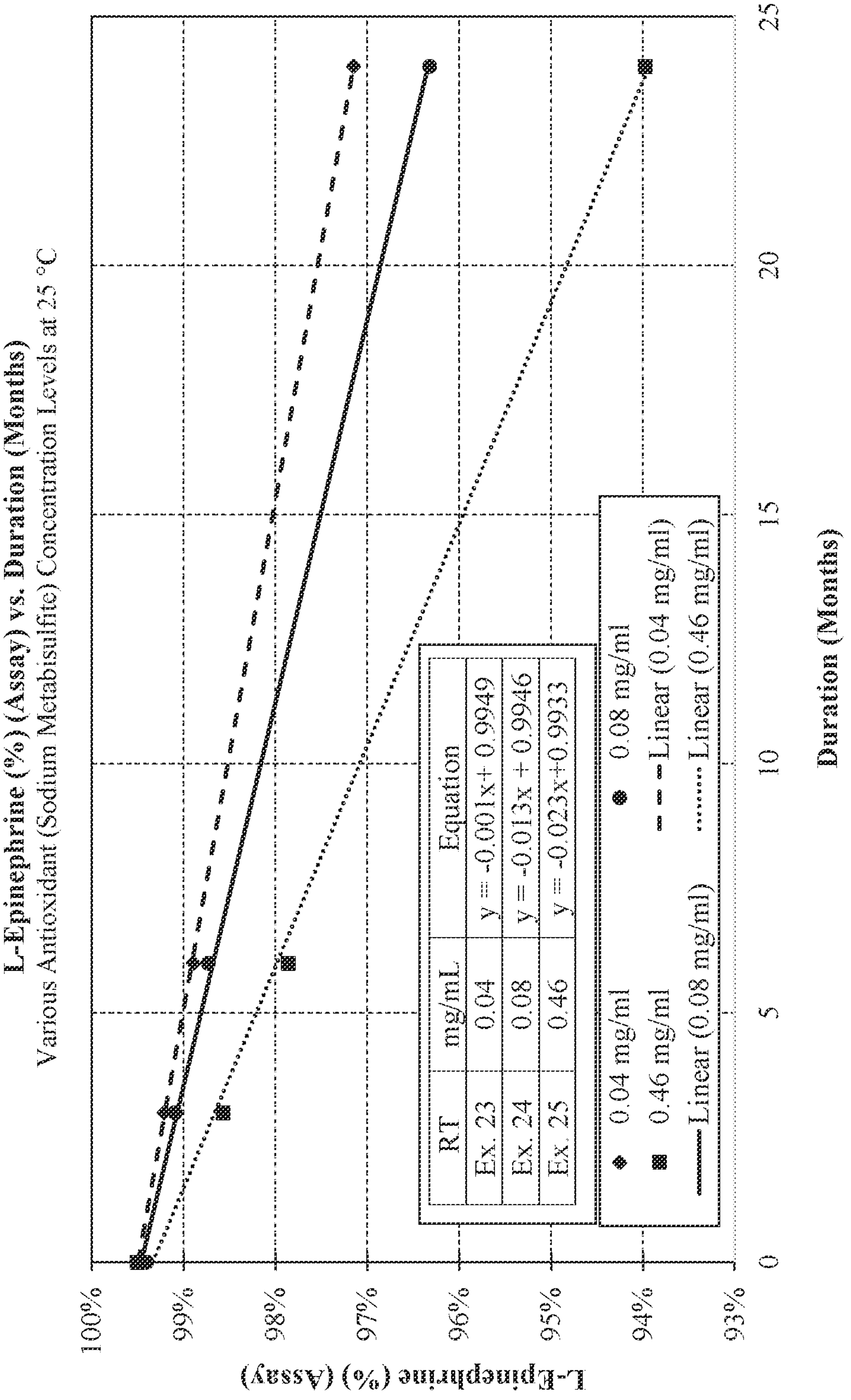
FIG. 8 depicts a graph showing L-epinephrine (%) recovery over time for Examples 23-25 at a storage temperature of 25° C.

FIG. 8 depicts L-epinephrine recovery for Examples 23-25 up to about 24 months at RT. As shown, L-epinephrine recovery at 24 months RT is greater than 96% for both Examples 23 and 24, whereas L-epinephrine recovery at 24 months RT for Example 25 is around 94%.

Figure 9:
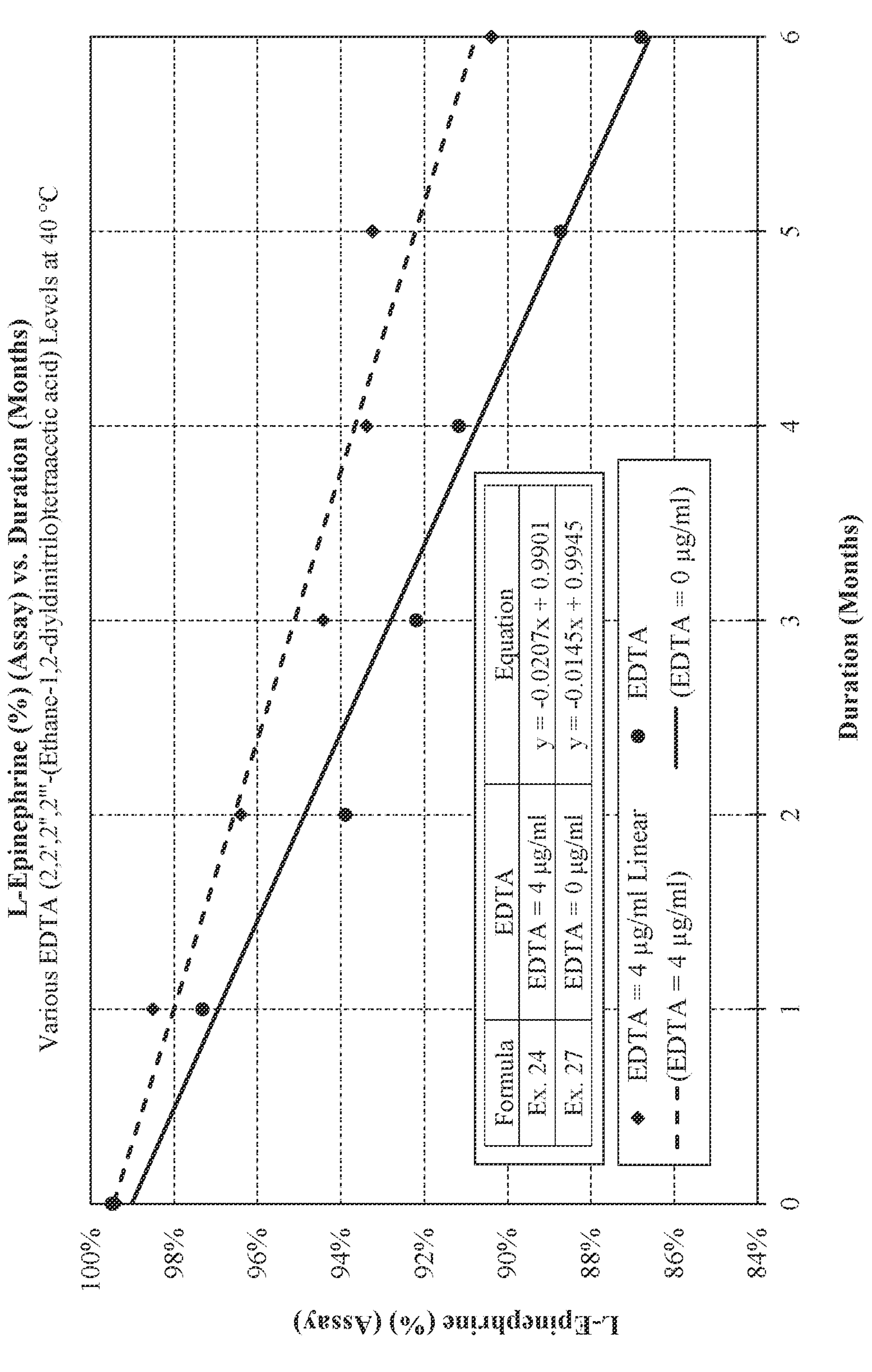
FIG. 9 depicts a graph showing L-epinephrine (%) recovery over time for Example 24 and Example 27 at a storage temperature of 40° C.

FIG. 9 depicts L-epinephrine (%) recovery for Example 24 as compared to Example 27. Notably, Examples 24 and 27 each contain the same amount of antioxidant (e.g., 0.08 mg/mL sodium metabisulfite), however Example 24 includes 4 µg/mL of EDTA while Example 27 does not include EDTA. As shown, at 6 months at 40° C., Example 24 has an L-epinephrine recovery of greater than 90%, whereas Example 27 has an L-epinephrine recovery amount of less than 88%.

Figure 10:
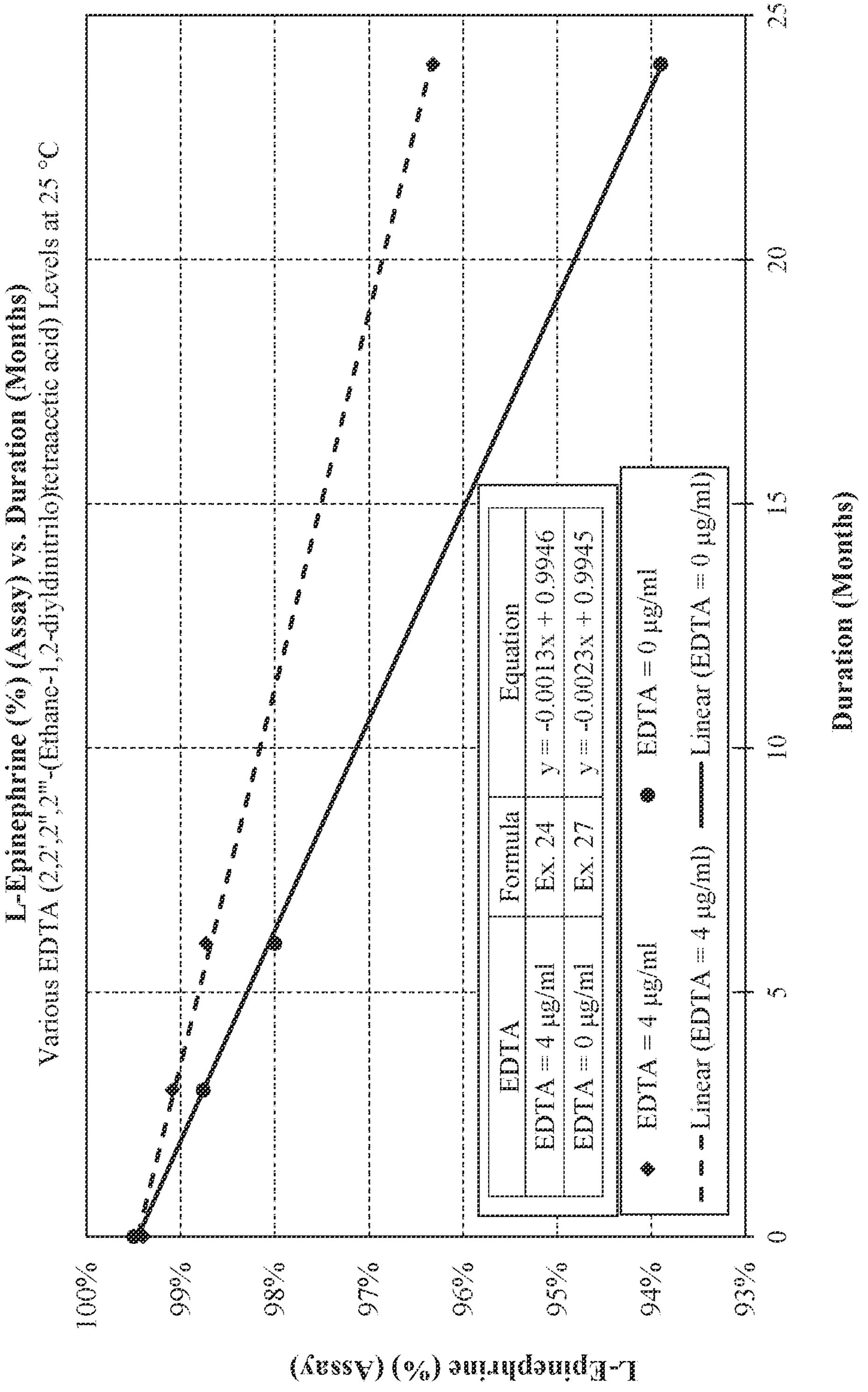
FIG. 10 depicts a graph showing L-epinephrine (%) recovery over time for Example 24 and Example 27 at a storage temperature of 25° C.

FIG. 10 depicts L-epinephrine recovery for Examples 24 and 27 up to about 24 months at RT. As shown, it is estimated that L-epinephrine recovery at 24 months RT is greater than 96% for Example 24, whereas L-epinephrine recovery at 24 months RT for Example 27 is around 94%.

Examples 30-34: Stability of 1 mg/mL Epinephrine Formulations

Example 30 was prepared under an atmosphere of nitrogen to provide an aqueous solution of L-Epinephrine (1 mg/mL), sodium chloride (6.15 mg/mL), sodium citrate dihydrate (2.0 mg/mL), citric acid monohydrate (2.0 mg/mL), EDTA (0.004 mg/mL), chlorobutanol (5.25 mg/mL) and sodium metabisulfite (0.04 mg/mL), and the pH of the aqueous solution was adjusted to pH 3.8 using HCl and NaOH. The aqueous solution was filtered through a 0.22 μm filter and the resultant solution was filled into a glass vial container having a rubber closure under nitrogen protection. Examples 31-33 were prepared in a manner similar to that described with respect to Example 30 except for using different concentrations of sodium metabisulfite (0.08, 0.24 and 0.457 mg/mL, respectively).

TABLE 7

1 mg/mL Epinephrine Formulations with varying amounts of antioxidant

| | Ingredient (mg/mL, or specified) | | Ex. 30 | Ex. 31 | Ex. 32 | Ex. 33 |
|---|---|---|---|---|---|---|
| 1 | API | L-Epinephrine, mg/mL | 1.0 | 1.0 | 1.0 | 1.0 |
| 2 | Antioxidant | Sodium metabisulfite, mg/mL | 0.04 | 0.08 | 0.24 | 0.457 |
| 3 | Preservative | Chlorobutanol | 5.25 | 5.25 | 5.25 | 5.25 |
| 3 | Metal-chelator | Disodium Edetate (EDTA), μg/mL | 0.004 | 0.004 | 0.004 | 0.004 |
| 4 | Tonicity | Sodium Chloride, mg/mL | 6.15 | 6.15 | 6.15 | 6.15 |
| 5 | buffer agent | Sodium citrate dihydrate, mg/mL | 2.0 | 2.0 | 2.0 | 2.0 |
| 6 | buffer agent | Citric acid monohydrate, mg/mL | 2.0 | 2.0 | 2.0 | 2.0 |
| | Tartaric acid | | 0 | 0 | 0 | 0 |
| | NaOH | | 0 | 0 | 0 | 0 |
| | pH | pH Unit | 3.8 | 3.8 | 3.8 | 3.8 |
| | Compounding Overage | | 0% | 0% | 0% | 0% |
| | API recovery, % (relative to API measured at 100% at 0 months at Room Temperature) | | | | | |
| | 60° C. at 1 week | | 97.1% | 96.7% | 96.0% | 94.8% |
| | 60° C. at 2 weeks | | 93.5% | 92.7% | 90.9% | 89.7% |
| | 60° C. at 3 weeks | | 89.5% | 88.2% | 85.5% | 83.1% |
| | 60° C. at 4 weeks | | 84.5% | 82.9% | 80.2% | 76.9% |
| | 40° C. 1 M | | 98.3% | 97.4% | 97.1% | 96.3% |
| | 40° C. 2 M | | 97.4% | 96.1% | 95.3% | 94.7% |
| | 40° C. 3 M | | 96.0% | 93.9% | 93.1% | 92.1% |
| | 40° C. 4 M | | 93.4% | 92.3% | 90.7% | 89.5% |
| | 40° C. 5 M | | 92.8% | 90.8% | 89.2% | 87.6% |
| | 40° C. 6 M | | 92.4% | 90.3% | 88.4% | 86.8% |
| | RT 3 M | | 99.3% | 98.3% | 98.1% | 97.8% |
| | RT 6 M | | 98.8% | 98.5% | 98.4% | 97.9% |
| | RT 24 M | | 97.1% | 96.6% | 95.1% | 94.2% |
| | Enantiomeric Impurity: D-Epinephrine (D-Epi) (w/w) | | | | | |
| | RT 0 | | 0.52% | 0.51% | 0.50% | 0.49% |
| | 60° C. at 1 week | | 2.57% | 2.17% | 1.53% | 1.21% |
| | 60° C. at 2 weeks | | 5.25% | 4.81% | 3.20% | 2.52% |
| | 60° C. at 3 weeks | | 8.88% | 8.01% | 6.21% | 4.82% |
| | 60° C. at 4 weeks | | 13.50% | 12.52% | 10.50% | 8.29% |
| | 40° C. 1 M | | 1.16% | 0.98% | 0.85% | 0.77% |
| | 40° C. 2 M | | 1.87% | 1.53% | 1.06% | 0.88% |
| | 40° C. 3 M | | 2.55% | 2.02% | 1.39% | 1.06% |
| | 40° C. 4 M | | 3.81% | 3.07% | 1.88% | 1.43% |
| | 40° C. 5 M | | 4.82% | 3.69% | 2.33% | 1.72% |
| | 40° C. 6 M | | 5.31% | 4.60% | 2.42% | 1.57% |
| | RT 3 M | | 0.56% | 0.51% | 0.49% | 0.46% |
| | RT 6 M | | 0.81% | 0.34% | 0.25% | 0.27% |
| | RT 24 M | | 2.06% | 1.30% | 1.10% | 0.97% |

Surprisingly and advantageously, the API recovery rates in Table 7 demonstrate that low amounts of antioxidant, such as (0.04 mg/mL-0.08 mg/mL) in combination with low amounts of EDTA are effective in reducing impurities.

In particular, as demonstrated in Table 7, Examples 30-33 exhibited API recoveries was as high as 97.9%-98.8% (w/w) at 6-months (RT).

Figure 11:
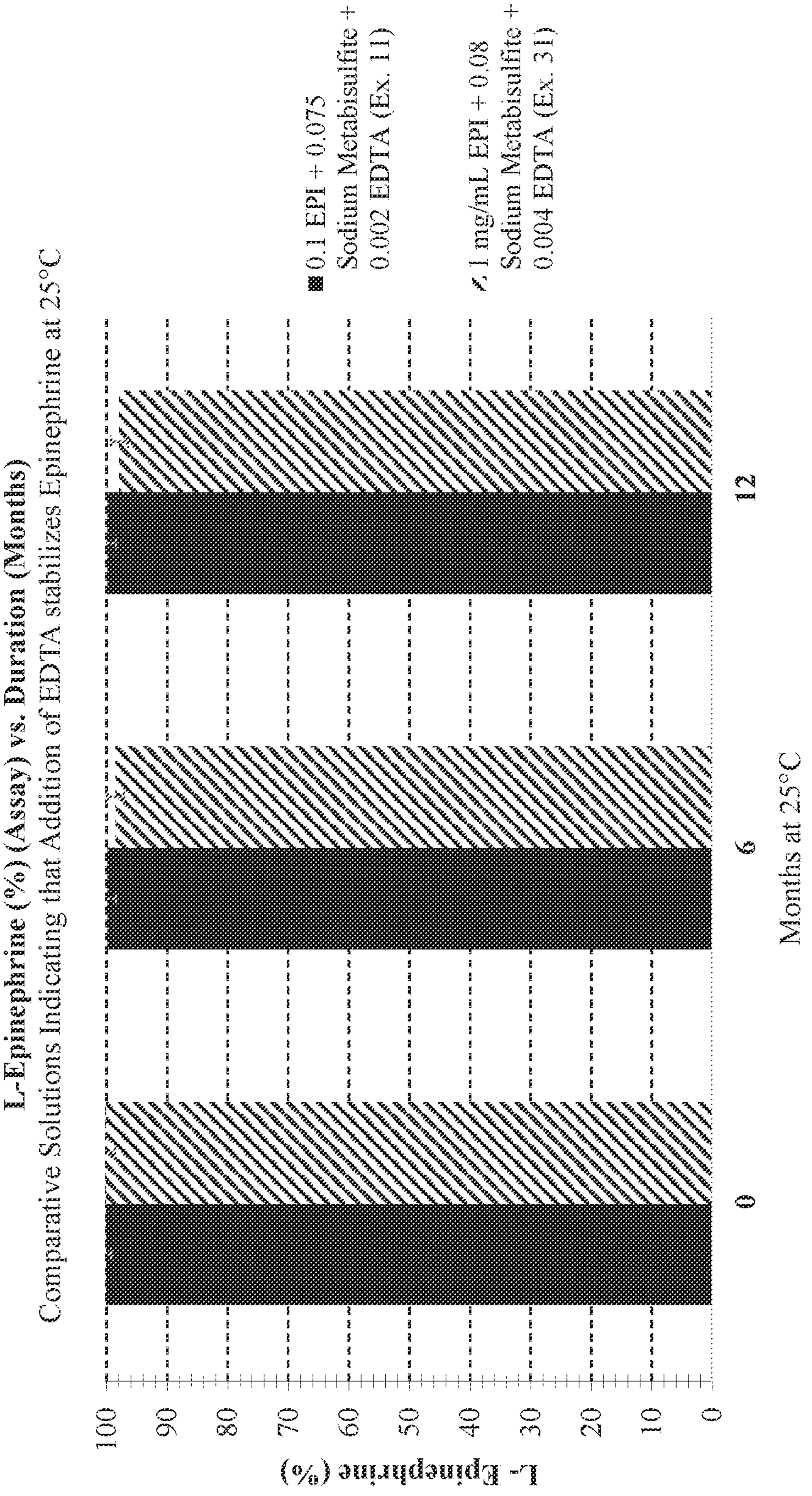
FIG. 11 depicts a graph showing L-epinephrine (%) recovery for Example 11 and Example 31 at different storage months at a storage temperature of 25° C.

FIG. 11 depicts a bar chart showing the L-epinephrine (%) w/w recovery for Example 11 (containing 0.1 mg/mL epinephrine provided with no overage) and Example 31 (containing 1 mg/mL epinephrine provided with no overage). As shown in FIG. 11, actual data was plotted and forecasted using data for 3 months, 6 months, and 24 months to generate an extrapolated value for 12 months of storage at RT, where L-epinephrine recovery is 97.9% for Example 31.

Figure 12:
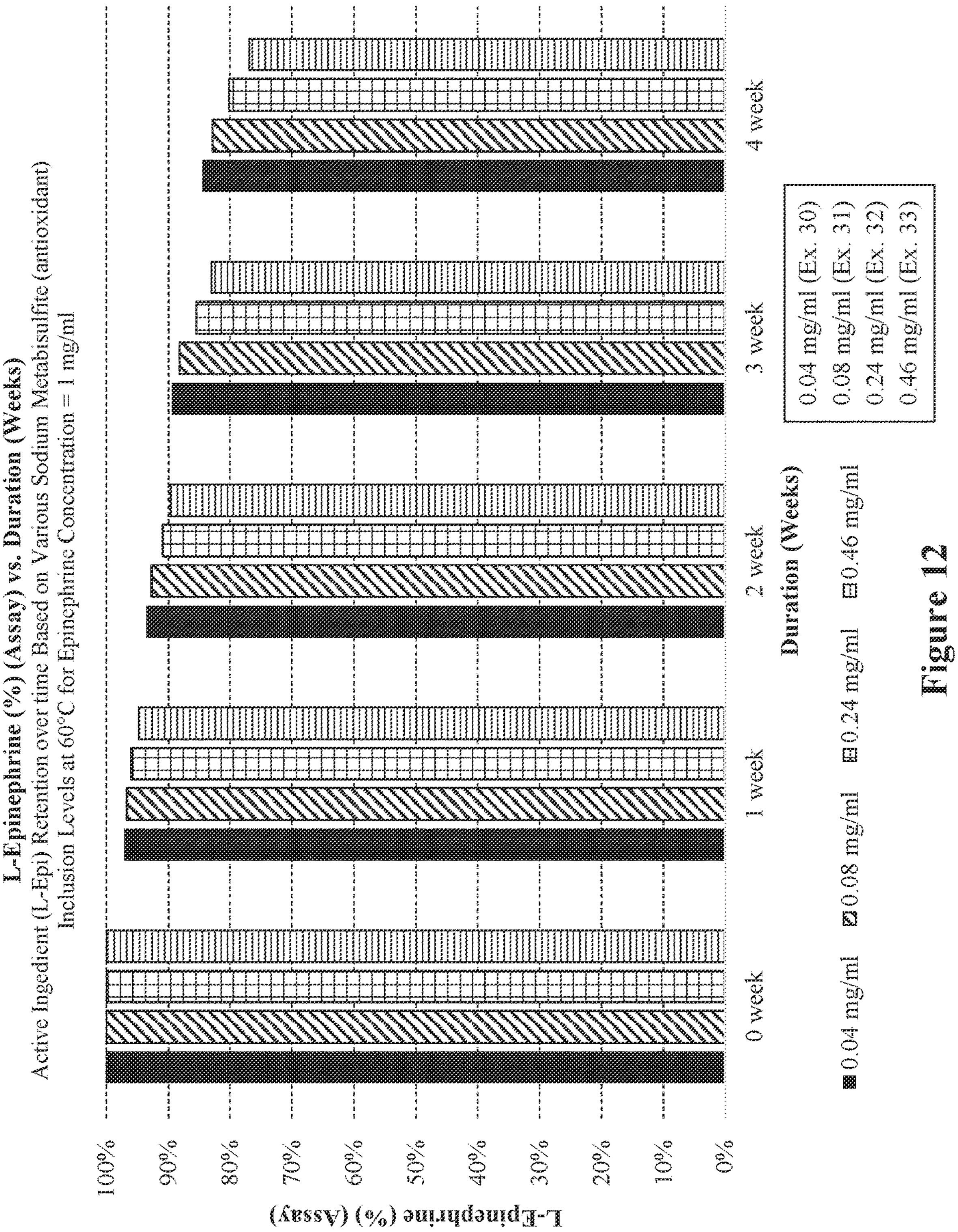
FIG. 12 depicts a graph showing L-epinephrine (%) recovery for Examples 30-33 at different storage times at a storage temperature of 60° C.

FIG. 12 depicts a bar chart showing the L-epinephrine (%) w/w recovery for Examples 30-33. As shown, at 4 weeks storage at a temperature of 60° C., Examples 30-31 have L-epinephrine recoveries above 80%, whereas Examples 32-33 have L-epinephrine recoveries at or lower than 80%.

Figure 13:
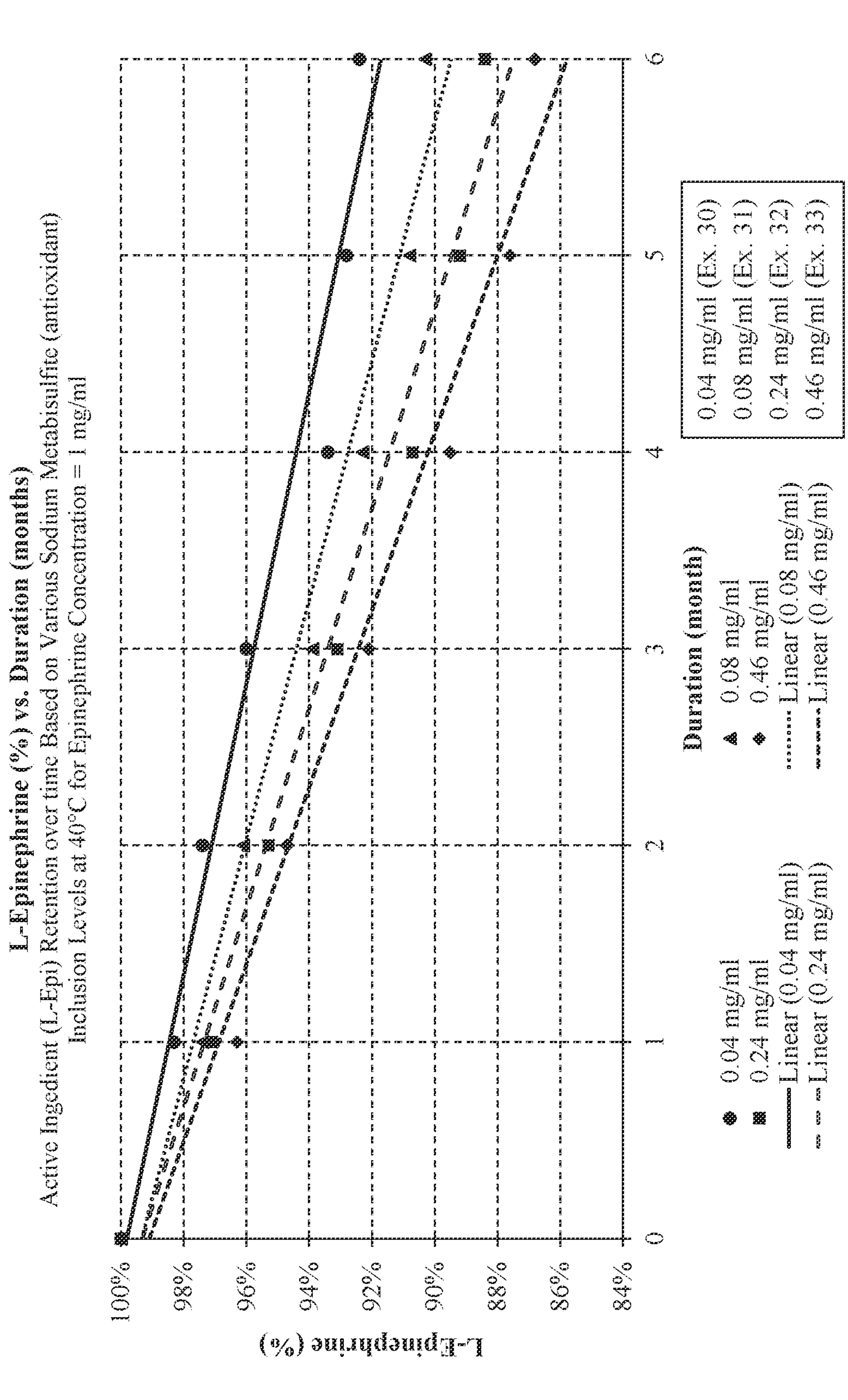
FIG. 13 depicts a graph showing L-epinephrine (%) recovery for Examples 30-33 over time at a storage temperature of 40° C.

FIG. 13 depicts a graph showing the L-epinephrine (%) w/w recovery for Examples 30-33 at a storage at a temperature of 40° C. for up to 6 months. As shown, Examples 30-31 have L-epinephrine recoveries above 88%, whereas Examples 32-33 have L-epinephrine recoveries at about or lower than 88%, such as at about or lower than 86% for Example 33.

Figure 14:
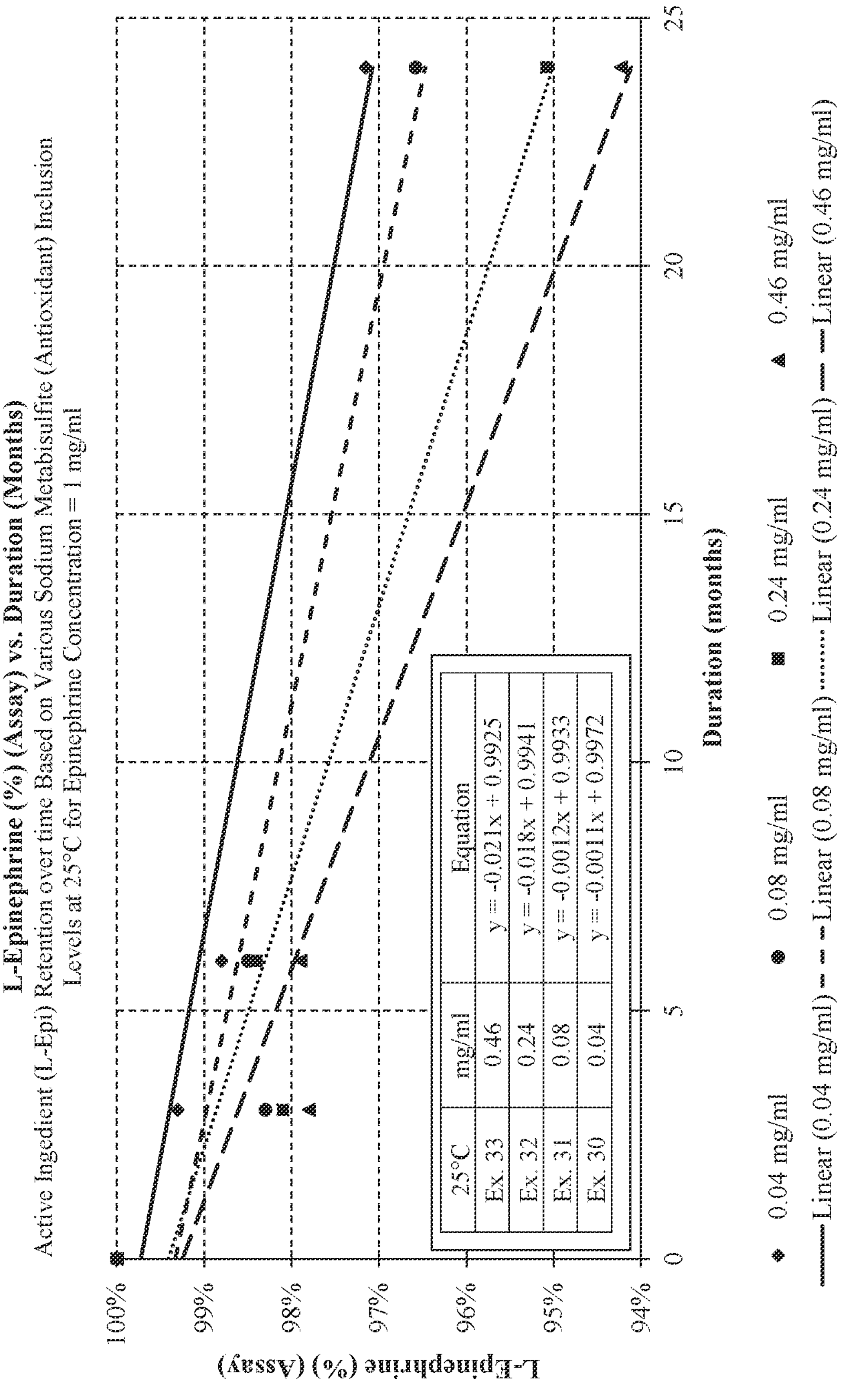
FIG. 14 depicts a graph showing L-epinephrine (%) recovery for Examples 30-33 over time at a storage temperature of 25° C.

FIG. 14 depicts L-epinephrine recovery for Examples 30-33 up to 24 months at RT. As shown, L-epinephrine recovery at 24 months RT is greater than 96% for both Examples 30 and 31, whereas L-epinephrine recovery at 24 months RT for Examples 32 and 33 is under 96%, around 95% and 94%, respectively.

Example 34: Epinephrine Pharmaceutical Formulation Having Low EDTA-Bound Zinc This is a prophetic example. The epinephrine formulations of the present disclosure are formulated to include relatively lower amounts of metal chelating agents (e.g., EDTA) as compared to certain other formulations. Lower amounts of EDTA is uniquely beneficial with regard to reducing undesirable zinc binding within the human body. Mechanistically, EDTA chemically interacts with zinc, e.g., zinc ions, to form coordination complexes that include a central atom or ion, e.g., a metallic ion, which is surrounded by an array of bound molecules or ions that are known as either ligands or complexing agents. Here, EDTA forms such metal-ligand chemical coordination complexes with zinc ions in the human body. As a result, higher levels of EDTA results in correspondingly higher levels of EDTA-zinc binding within the human body. This phenomena is generally undesirable, since most persons need to maintain some minimum zinc level throughout the day. The undesirable binding with zinc in the human body can be controlled and decreased relative to other epinephrine formulations having relatively higher levels of EDTA. For instance, while the diet may provide more than enough zinc to meet daily recommended amounts, other environmental factors, or internal factors, such as reactions with medicines in the body can reduce the bioavailability of zinc. For instance, N. Roohani et al. estimate that human zinc intake ranges from about 6.9-15.1 mg/day of zinc, however human total absorbed zinc ranges from 0.85-6.4 mg/day. [Roohani N., Hurrell R., Kelishadi R. Schulin R. Zinc and its importance for human health: An integrative review. *J Res Med Sci.* 2013 February; 18(2): 144-57. PMID: 23914218; PMCID: PMC3724376.]

As shown below, the amount of bound zinc to EDTA was calculated. An example calculation of 10 μg/mL is provided herein. Using 10 μg/mL of EDTA-disodium as an example, the amount of bound zinc to 10 μg/ml of EDTA-disodium can be calculated according to the following example:

1. Molecular weight of EDTA-disodium is 336.21 g/mol.
2. The mole number of 10 μg of EDTA-disodium is 10 μg/336.21 g/mol=0.0297 μmol.
3. One molecular of EDTA-disodium binds to one molecular of zinc.
4. Molecular weight of zinc is 65.38 g/mol.
5. Therefore, 10 μg of EDTA-disodium binds to 0.0297 μmol×65.38 g/mol=1.9 μg.

The corresponding EDTA concentrations for 1 μg/mL up to 20 μg/mL were calculated according to the 10 μg/mL example as described above and are shown in the Table below.

TABLE 8

| EDTA Concentration Level (μg/mL) | Zinc Bound to EDTA (μg/mL) |
|---|---|
| 1 | 0.19 |
| 2 | 0.4 |
| 4 | 0.8 |
| 8 | 1.6 |
| 10 | 1.9 |
| 20 | 3.9 |

Table 8 indicates that higher amounts of EDTA correlates with higher levels of zinc binding to EDTA. As shown above in Table 8, the presently disclosed epinephrine formulations include anywhere between 1 μg/mL to about 8 μg/mL of EDTA, which can correspondingly bind with anywhere from 0.19 μg/mL to about 1.6 μg/mL of zinc, respectively. The upper binding limit of 1.6 μg/mL of zinc is relatively minor compared to the total amount of zinc humans can absorb per day, which ranges from 0.85 mg/day-6.4 mg/day. In this way, the relatively low levels of EDTA included in the disclosed formulations do not undesirably bind with excessive levels of zinc in the human body. As a result, these low levels of EDTA in the presently disclosed formulations do not interfere with normal healthy human zinc absorption on a daily basis, and thereby do not contribute to zinc deficiency.

Figure 15:
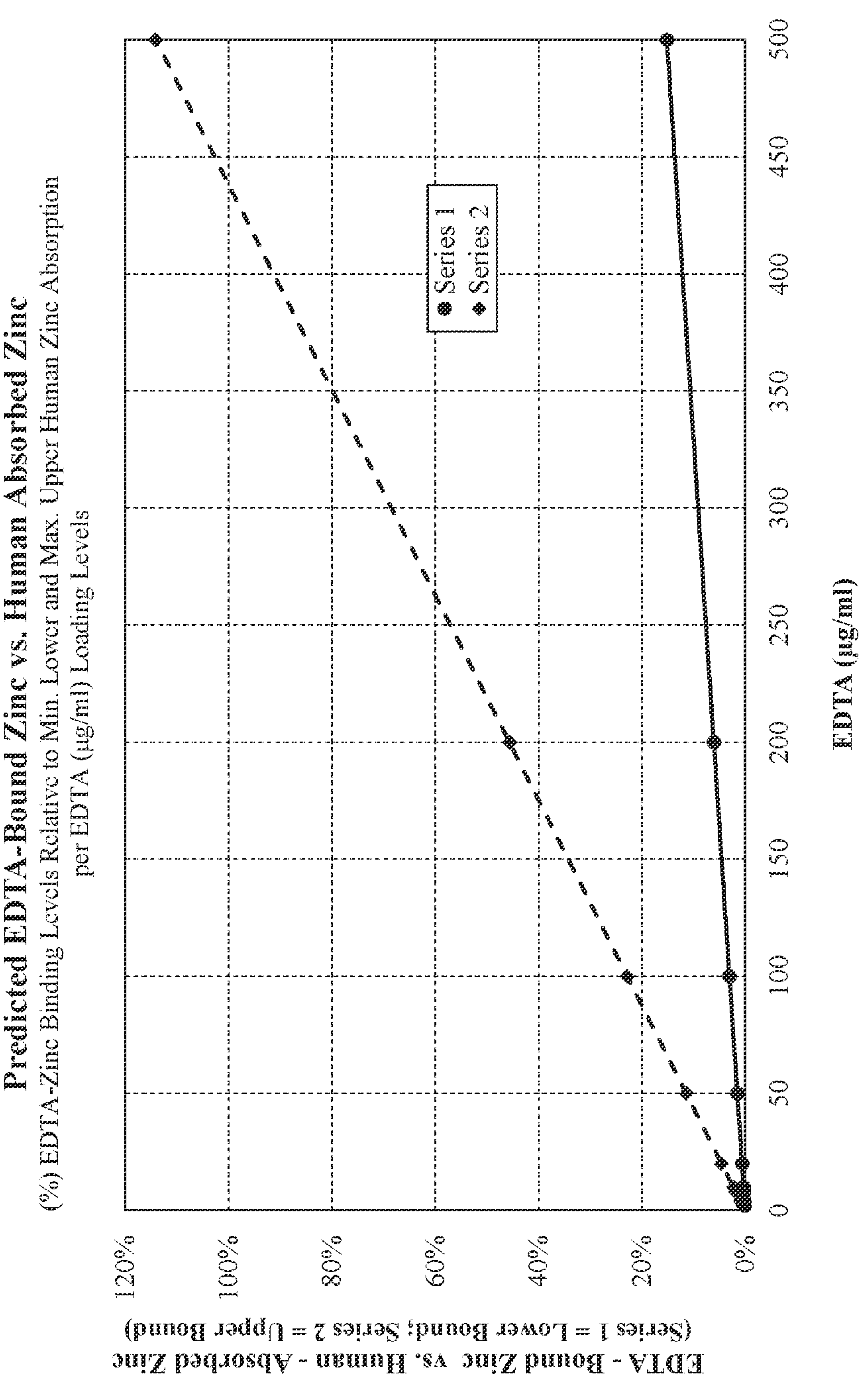
FIG. 15 is a prophetic example depicting a graph showing EDTA-bound zinc vs. Human-absorbed zine over EDTA concentration.

FIG. 15 depicts a graph comparing upper and lower bounds of EDTA-bound zinc in the human body relative to EDTA concentration levels. The upper bounds and lower bounds can be calculated according to the following procedure for 10 μg/mL EDTA (e.g., if EDTA-disodium is at a concentration level of 10 μg/mL and the patient receives an injection of 10 mL of 10 μg/mL EDTA-disodium in a day):

Total EDTA-disodium is calculated as: 10 μg/mL×10 mL=100 μg.

As provided above, 10 μg of EDTA-disodium absorbs 1.9 μg zinc, so 100 μg of EDTA-disodium will absorb zinc=1.9 μg×10=19 μg of zinc.

Based on Roohani et al., human absorbed zinc may range between 0.85 mg/mL-6.4 mg/mL per day (e.g., indicating that safe human zinc levels are known to remain between 0.85 mg/mL-6.4 mg/mL per day).

As a result, 19 μg of EDTA-bound zinc divided by the maximum amount of 6.4 mg of human absorbed zinc (Series 1=Lower Bound)=19 μg zinc/6.4 mg zinc=0.00296=0.3% (Series 1=Lower Bound)

Likewise, 19 μg of EDTA-bound zinc divided by the minimum amount of 0.85 mg of human absorbed zinc (Series 2=Upper Bound)=19 μg zinc/0.85 mg zinc=0.022=2.2% (Series 2=Upper Bound).

These calculations were used to calculate upper and lower bounds of EDTA-bound zinc versus human-absorbed zinc. As shown in FIG. 15, EDTA-bound zinc for 0-8 μg EDTA (e.g., as included in several of the presently disclosed formulations) has a negligible impact on zinc removal from the human body and may thereby be viewed as desirable. For example, a corresponding calculation produces the following: 8 μg EDTA absorbs 1.6 μg zinc; 1.6 μg zinc/0.85 mg (minimum amount of zinc recommended in the human body)=1.88% (Series 2=Upper Bound).

This means that an epinephrine formulation including 8 μg EDTA reduces zinc levels in the human body by only a maximum of 1.88%, which can be considered negligible. However, this loading level of 8 μg EDTA is still associated with various favorable and unexpected results as indicated by one or more of the disclosed Examples or Figures, including increased API retention over time due to decreased oxidation as may be catalyzed by, for example, iron ions prevalent in the headspace of a storage vial or stopper of the vial. More specifically, this relatively minor level (e.g., 8 μg EDTA) of EDTA still removes sufficient iron ions to decrease associated catalysis of phenol oxidation, thereby contributing to increased API retention over time. In addition, 8 μg EDTA only has a negligible effect on zinc reduction (e.g. 1.88% as calculated here) in the human body due to zinc-binding, and can thereby be deemed safe for usage.

These and other modifications and variations of the present disclosure may be practiced by those of ordinary skill in the art, without departing from the spirit and scope of the present disclosure. In addition, it should be understood that aspects of the various embodiments may be interchanged in whole or in part. Furthermore, those of ordinary skill in the art will appreciate that the foregoing description is by way of example only, and is not intended to limit the disclosure so further described in such appended claims.

What is claimed is:

1. A pharmaceutical formulation comprising:

1 mg/mL of an active pharmaceutical ingredient (API) comprising epinephrine or a pharmaceutically acceptable salt thereof;

between 0.04 mg/mL and 0.08 mg/mL of an antioxidant comprising sodium metabisulfite;

between 5 mg/mL and 7 mg/mL of a tonicity regulating agent, the tonicity regulating agent configured to regulate an osmolality of the pharmaceutical formulation between 210 milliosmoles per kilogram (mOsmol/kg) and 300 mOsmol/kg;

a pH-stabilizing buffer system including 2 mg/mL of citric acid and 2 mg/mL of sodium citrate configured to maintain a pH level of the pharmaceutical formulation at 3.8; and a preservative comprising chlorobutanol;

wherein the pharmaceutical formulation is configured to have an API recovery of greater than about 96% after storage at a temperature of 25° C.±2° C. for 24 consecutive months, and wherein the pharmaceutical formulation is formulated for parenteral administration.

2. The pharmaceutical formulation of claim 1, wherein the pharmaceutical formulation is configured to be administered intravenously, subcutaneously, or intramuscularly.

3. The pharmaceutical formulation of claim 1, wherein the tonicity regulating agent comprises sodium chloride.

4. The pharmaceutical formulation of claim 1, comprising 6.15 mg/ml of the tonicity regulating agent.

5. The pharmaceutical formulation of claim 1, comprising 5.25 mg/mL of chlorobutanol.

6. The pharmaceutical formulation of claim 1, wherein the pharmaceutical formulation is configured to have an API recovery of about 98.5% or greater after storage at a temperature of 25° C.±2° C. for six consecutive months.

7. The pharmaceutical formulation of claim 1, wherein the pharmaceutical formulation is configured to have an API recovery of 90% or greater after storage at a temperature of about 40° C.±2° C. for six consecutive months.

8. The pharmaceutical formulation of claim 1, wherein the pharmaceutical formulation does not contain tartrate and its salts, acids, or bases thereof.

9. A pre-filled syringe containing a pharmaceutical formulation, the pharmaceutical formulation comprising:

1 mg/mL of an active pharmaceutical ingredient (API) comprising epinephrine or a pharmaceutically acceptable salt thereof;

between 0.04 mg/mL and 0.08 mg/mL of an antioxidant comprising sodium metabisulfite;

between 5 mg/mL and 7 mg/mL of a tonicity regulating agent, the tonicity regulating agent configured to regulate an osmolality of the pharmaceutical formulation between 210 milliosmoles per kilogram (mOsmol/kg) and 300 mOsmol/kg;

a pH-stabilizing buffer system including 2 mg/mL of citric acid and 2 mg/mL of sodium citrate configured to maintain a pH level of the pharmaceutical formulation at 3.8; and a preservative comprising chlorobutanol;

wherein the pharmaceutical formulation is configured to have an API recovery of greater than about 96% after storage at a temperature of 25° C.±2° C. for 24 consecutive months, and wherein the formulation is formulated for injection.

10. The pre-filled syringe of claim 9, wherein the pharmaceutical formulation is configured to be administered intravenously, subcutaneously, or intramuscularly.

11. The pre-filled syringe of claim 9, wherein the tonicity regulating agent comprises sodium chloride.

12. The pre-filled syringe of claim 9, comprising 6.15 mg/mL of the tonicity regulating agent.

13. The pre-filled syringe of claim 9, comprising 5.25 mg/mL of chlorobutanol.

14. The pre-filled syringe of claim 9, wherein the pharmaceutical formulation is configured to have an API recovery of about 98.5% or greater after storage at a temperature of 25° C.±2° C. for six consecutive months.

15. The pre-filled syringe of claim 9, wherein the pharmaceutical formulation is configured to have an API recovery of 90% or greater after storage at a temperature of about 40° C.±2° C. for six consecutive months.

16. The pre-filled syringe of claim 9, wherein the pharmaceutical formulation does not contain tartrate and its salts, acids, or bases thereof.

17. A formulation configured to be administered as a single dose from a pre-filled 10 milliliter (mL) syringe, each single dose comprising:

1 mg/mL of an active pharmaceutical ingredient (API) comprising epinephrine or a pharmaceutically acceptable salt thereof;

between 0.04 mg/mL and 0.08 mg/mL of an antioxidant comprising sodium metabisulfite;

between 5 mg/mL and 7 mg/mL of a tonicity regulating agent, the tonicity regulating agent configured to regulate an osmolality of the formulation between 210 milliosmoles per kilogram (mOsmol/kg) and 300 mOsmol/kg;

a pH-stabilizing buffer system including 2 mg/mL of citric acid and 2 mg/mL of sodium citrate configured to maintain a pH level of the formulation with a range of 3.5 to 5.0; and a preservative comprising chlorobutanol;

wherein the formulation is configured to have an API recovery of greater than about 96% after storage at a temperature of 25° C.±2° C. for 24 consecutive months, and wherein the formulation is formulated for injection.

18. The formulation of claim 17, comprising 5.25 mg/mL of chlorobutanol.

19. The formulation of claim 17, wherein the formulation is configured to have an API recovery of about 98.5% or greater after storage at a temperature of 25° C.±2° C. for six consecutive months.

20. The formulation of claim 17, wherein the formulation is configured to have an API recovery of 90% or greater after storage at a temperature of about 40° C.±2° C. for six consecutive months.

21. The formulation of claim 17, wherein the formulation does not contain tartrate and its salts, acids, or bases thereof.

* * * * *